United States Patent [19]
Mattson et al.

[11] Patent Number: 5,387,593
[45] Date of Patent: Feb. 7, 1995

[54] PIPERAZINYL- AND PIPERIDINYL-CYCLOHEXANOLS

[75] Inventors: Ronald J. Mattson, Meriden; John D. Catt, Southington, both of Conn.

[73] Assignee: Briston-Myers Squibb, New York, N.Y.

[21] Appl. No.: 198,165

[22] Filed: Feb. 17, 1994

Related U.S. Application Data

[63] Continuation-in-part of Ser. No. 952,229, Sep. 28, 1992, abandoned, which is a continuation-in-part of Ser. No. 806,989, Dec. 13, 1991, abandoned.

[51] Int. Cl.$^6$ ............... H61K 31/445; C07D 401/10; C07D 403/10; C07D 211/14
[52] U.S. Cl. .................... 514/326; 514/252; 514/253; 514/255; 514/317; 514/318; 514/321; 514/331; 544/360; 544/364; 544/372; 544/377; 544/379; 544/389; 544/396; 544/398; 544/399; 544/400; 546/192; 546/194; 546/197; 546/208; 546/213; 546/214; 546/232; 546/234; 546/236; 546/237; 546/240; 549/341; 549/445; 568/329
[58] Field of Search ............... 546/194, 197, 208, 213, 546/214, 234, 236, 240, 232; 514/317, 318, 321, 326, 331

[56] References Cited

U.S. PATENT DOCUMENTS
3,965,180  6/1976  Lednicer ........................ 546/236

OTHER PUBLICATIONS
Mattson et al, *Chemical Abstracts*, vol. 119, No. 180667 (Abstract for EP 546583, Jun. 16, 1993) (1993).
Mattson et al, *Chemical Abstracts*, vol. 120, No. 45972 (Abstract for EP 560669, Sep. 15, 1993) (1994).

*Primary Examiner*—Emily Bernhardt
*Attorney, Agent, or Firm*—Sandra M. Nolan

[57] ABSTRACT

Novel piperazinyl- and piperidinyl-cyclohexanols of the following formula are useful as anxiolytic agents and have other psychotropic properties

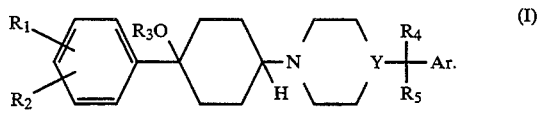

24 Claims, No Drawings

PIPERAZINYL- AND PIPERIDINYL-CYCLOHEXANOLS

CROSS REFERENCE TO RELATED PATENT

This application is a continuation-in-part of copending application U.S. Ser. No. 07/952,229, filed Sep. 28, 1992 and now abandoned, which is a continuation-in-part of U.S. Ser. No. 07/806,989, filed Dec. 13, 1991 now abandoned.

BACKGROUND OF THE INVENTION

This invention generally pertains to piperazinyl- and piperidinyl-cyclohexanol compounds having anxiolytic and other psychotropic, bioaffecting properties and to their preparation and use. In some preferred embodiments, the invention is concerned with 1,4-disubstituted piperazine or piperidine derivatives wherein the 4-substituent is benzyl or substituted benzyl, and the 1-substituent is 4-aryl-4-hydroxycyclohexyl or 4-aryl-4-alkoxycyclohexyl moiety. These compounds and others structurally related thereto possess a unique serotonergic profile that makes them useful in the treatment of anxiety. Caprathe et al disclosed a series of piperazinyl-cyclohexanol compounds characterized by structural Formula A in U.S. Pat. No. 4,957,921. Formula A is:

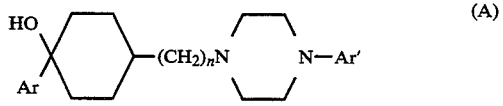

wherein n is 0 to 4 and Ar and Ar' are aryl or heterocyclic rings.

As can be seen, these earlier compounds are chemically distinguishable from the instant compounds on the basis of their chemical structures because they are aryl- or heteroaryl-piperazines, whereas the instant compounds are benzyl- or heteroarylmethyl-piperazines (when, in Formula I below, Y=N) or piperidines (when, in Formula I below, Y=CH). Additionally, these earlier compounds are biologically distinguishable from the instant compounds, since they possess dopaminergic properties, which are associated with undesirable side effects including Parkinsonism and extrapyramidal side effects such as catalepsy. Contrastingly, the instant compounds are serotonergic agents devoid of dopaminergic properties and the movement disorders often associated therewith.

Caprathe et al disclosed a series of piperazinyl-cyclohexene compounds characterized by structural formula B in U.S. Pat. No. 4,975,445. Formula B is:

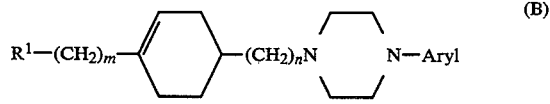

wherein $R^1$ is an aryl or heterocyclic ring, m is 0–2 and n is 0–4. Likewise, these compounds are structurally and biologically distinguishable from the instant compounds. Chemically, the reference compounds are aryl-piperazines, while the instant compounds are benzyl- or heteroarylmethyl-piperazines. Biologically, their dopaminergic properties distinguish them from applicants' compounds, which have serotonergic activity. Accordingly, the movement disorders associated with dopaminergic agents are avoided when the instant compounds are administered.

SUMMARY AND DETAILED DESCRIPTION OF THE INVENTION

In its broadest aspect, the invention is concerned with certain compounds which are substituted benzyl- or heteroarylmethyl-piperazinyl cyclohexanes or substituted benzyl or heteroarylmethyl piperidinyl cyclohexanes which are useful anxiolytic agents. The compounds conform to Formula I:

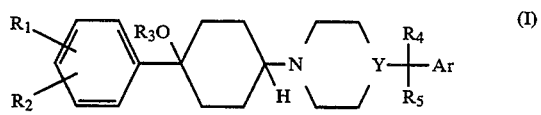

wherein $R_1$ and $R_2$ are selected independently from H, halogen, $CF_3$ or $C_{1-4}$ alkoxy groups except that $R_1$ and $R_2$ cannot both be H simultaneously; and $R_1$ and $R_2$, when on adjacent carbon atoms, can be taken together to form a

bridge (n=1–3); $R_3$ is H or $C_{1-4}$ alkyl; $R_4$ and $R_5$ are independently selected from H, $C_{1-4}$ alkyl or phenyl; Y is N or CH; and Ar is a heteroaryl ring or a substituted or unsubstituted phenyl ring.

Compounds of formula I include all pharmaceutically acceptable salts and/or solvates thereof. The invention also encompasses all stereoisomers of compounds of Formula I.

Pharmaceutically acceptable salts based on Formula I can be obtained using inorganic or organic acids such as sulfuric, phosphoric, hydrochloric, hydrobromic, hydroiodic, citric, acetic, benzoic, fumaric, cinnamic, mandelic, nitric, mucic, isethionic, palmitic, heptanoic and the like.

$R_1$ and $R_2$ may, either singly or in combination, be halogen atoms. Preferred halogens are Cl and F, with F being highly preferred.

While $R_1$ and $R_2$ may both be $C_{1-4}$ alkoxy moieties, it is generally preferred that only one of them be alkoxy. Preferred alkoxy groups are those that contain not more than two carbon atoms. Thus, methoxy and ethoxy groups are preferred embodiments for $R_1$ and $R_2$.

Compounds in which one of $R_1$ and $R_2$ is F and the other is $OCH_3$ are very useful.

$R_1$ and $R_2$, when on adjacent carbon atoms, may be taken together to form a bridging group. It is preferred that the group be a 3- to 5- membered group containing 2 terminal oxygen atoms separated by a —$(CH_2)_n$—(n=1–3) linkage. Compounds having

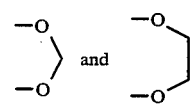

bridges are highly preferred.

$R_3$ may be H or a $C_{1-4}$ alkyl moiety. It is preferred that $R_3$ be H or contain no more than two carbon atoms.

Accordingly, it is preferred that $R_3$ be H, $CH_3$ or $C_2H_5$, with H and $CH_3$ being highly preferred.

$R_4$ and $R_5$ are, as indicated above, selected independently from H, $C_{1-4}$ alkyl and phenyl moieties. It is preferred that at least one of $R_4$ and $R_5$ be H, with the other being H or $C_{1-2}$ alkyl (i.e., H, $CH_3$ or $C_2H_5$). It is highly preferred that both $R_4$ and $R_5$ be H, so that a methylene bridge is formed between the piperazine (Y=N) or piperidine (Y=CH) ring and the Ar group.

Y may be N or CH. While it may be either, the use of piperidines (wherein Y=CH) is preferred.

Ar may be any of a variety of compounds based upon a phenyl or heteroaryl ring. Useful heteroaryl groups include 2-thienyl, 2-furanyl and 1-methyl-2-pyrrolyl moiety.

Ar may also be an unsubstituted phenyl group or a substituted phenyl group of Formula II:

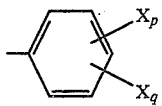

(II)

wherein $X_p$ and $X_q$ may be halogen (preferably Cl or F), nitro, amino, carboxamide, $C_{1-4}$ alkyl, $C_{1-4}$ alkoxy, $C_{1-4}$ haloalkyl, $C_{1-4}$ alkylthio or similar moieties, or $X_p$ and $X_q$ can be taken together to form a

bridge (n=1-3). The values p and q may be 0 to 5, with p+q<5.

Ar may also be a heteroaryl group. Suitable heteroaryl groups contain O, S and/or N atoms and include 3- and 4-pyridinyl, 2-thienyl, 2-furanyl, and 1-methyl-2-pyrrolyl and similar moieties.

There are several groups of preferred compounds that fall within formula I.

One group is those compounds in which $R_1$=F, $R_2$ and $R_3$=H, and $X_p$=H, F, Cl, Br, or $OCH_3$.

A second group is that in which $R_1$=F, $R_2$ and $R_3$=H and $X_p$ and $X_q$=F.

Another group is made up of those compounds in which $R_1$ and $R_2$ form an —$OCH_2O$— bridge and at least one of $X_p$ and $X_q$ is F or $OCH_3$.

Yet another group consists of molecules in which $R_1$ and $R_2$ form a —$OCH_2O$— bridge, $R_3$=$C_1$, and $X_p$ and $X_q$ are both F.

Two highly preferred groups of compounds are those in which either:

(a) $R_1$ and $R_2$ form a —$OCH_2O$— bridge and $X_p$ is F or $OCH_3$; or (b) $R_1$ or $R_2$ is F or $CF_3$ and at least one of $X_p$ and $X_q$ is F.

Preferred compounds of Formula I include:

Z-1-(1,3-benzodioxol-5-yl)-4-[4-(phenylmethyl)-1-piperidinyl]cyclohexanol;
Z-1-(4-methoxyphenyl)-4-[4-(phenylmethyl)-1-piperidinyl]cyclohexanol;
Z-1-(1,3-benzodioxol-5-yl)-4-[4-(phenylmethyl)-1-piperazinyl)cyclohexanol;
Z-1-(4-methoxyphenyl)-4-[4-(phenylmethyl)-1-piperazinyl]cyclohexanol;
Z-1-[4-(1,3-benzodioxol-5-yl)-4-methoxycyclohexyl]-4-(phenylmethyl)-piperazine;
Z-1-(1,4-benzodioxan-6-yl)-4-[4-(phenylmethyl)-1-piperazinyl]cyclohexanol;
E-1-(1,4-benzodioxan-6-yl)-4-[4-(phenylmethyl)-1-piperazinyl]cyclohexanol;
Z-1-(1,3-benzodioxol-5-yl)-4-[4-[(3-methoxyphenyl)methyl]-1-piperazinyl]cyclohexanol;
Z-1-(1,3-benzodioxol-5-yl)-4-[4-[(3-fluorophenyl)methyl]-1-piperazinyl]cyclohexanol;
Z-1-(1,3-benzodioxol-5-yl)-4-[4-[(2-fluorophenyl)methyl]-1-piperazinyl]cyclohexanol;
Z-1-(1,3-benzodioxol-5-yl)-4-[4-[(2-methylphenyl)methyl]-1-piperazinyl]cyclohexanol;
Z-1-(1,3-benzodioxol-5-yl)-4-[4-[(2-nitrophenyl)methyl]-1-piperazinyl]cyclohexanol;
Z-1-(1,3-benzodioxol-5-yl)-4-[4-[(2-chlorophenyl)methyl]-1-piperazinyl]cyclohexanol;
Z-1-(1,3-benzodioxol-5-yl)-4-[4-(2-thienylmethyl)-1-piperazinyl]cyclohexanol;
Z-1-(1,3-benzodioxol-5-yl)-4-[4-[(2,5-dichlorophenyl)methyl]-1-piperazinyl]cyclohexanol;
Z-1-(1,3-benzodioxol-5-yl)-4-[4-[(2,5-difluorophenyl)methyl]-1-piperazinyl]cyclohexanol;
Z-1-(1,3-benzodioxol-5-yl)-4-[4-[(2,3-difluorophenyl)methyl]-1-piperazinyl]cyclohexanol;
Z-1-(1,3-benzodioxol-5-yl)-4-[4-[(3,5-difluorophenyl)methyl]-1-piperazinyl]cyclohexanol;
Z-1-(1,3-benzodioxol-5-yl)-4-[4-[(2-iodophenyl)methyl]-1-piperazinyl]cyclohexanol;
Z-1-(1,3-benzodioxol-5-yl)-4-[4-[(1,3-benzodioxo-4-yl)methyl]-1-piperazinyl]cyclohexanol;
Z-1-(4-fluorophenyl)-4-[4-[(3-methoxyphenyl)methyl]-1-piperazinyl]cyclohexanol;
Z-1-(4-fluorophenyl)-4-[4-[(2-chlorophenyl)methyl]-1-piperazinyl]cyclohexanol;
Z-1-(4-fluorophenyl)-4-[4-[(2,5-difluorophenyl)methyl]-1-piperazinyl]cyclohexanol;
Z-1-[(4-trifluoromethyl)phenyl]-4-[4-[(2-chlorophenyl)methyl]-1piperazinyl]cyclohexanol;
Z-1-[(4-trifluoromethyl)phenyl]-4-[4-[(3-methoxyphenyl)methyl]-1-piperazinyl]cyclohexanol;
Z-1-(1,3-benzodioxol-5-yl)-4-[4-[(2-fluoro-5-methoxyphenyl)methyl]-1-piperazinyl]cyclohexanol;
Z-1-(4-fluorophenyl)-4-[4-[(2-fluoro-5-methoxyphenyl)methyl]-1-piperazinyl]cyclohexanol;
Z-1-(1,4-benzodioxan-6-yl)-4-[4-[(3-methoxyphenyl)methyl]-1-piperidinyl]cyclohexanol;
Z-1-(1,3-benzodioxol-5-yl)-4-[4-[(3-methoxyphenyl)methyl]-1-piperidinyl]cyclohexanol;
Z-1-(1,3-benzodioxol-5-yl)-4-[4-[(2,5-difluorophenyl)methyl]-1-piperidinyl]cyclohexanol;
Z-1-]4-(1,3-benzodioxol-5-yl)-4-methoxy-1-cyclohexyl]-4-[(3-methoxyphenyl)methyl]piperidine;
Z-1-]4-(1,4-benzodioxan-6-yl)-4-methoxy-1-cyclohexyl]-4-[3-(methoxypheny)methyl]-piperidine fumarate;)
Z-1-]4-(1,3-benzodioxol-5-yl)-4-methoxy-1-cyclohexyl]-4-[(2,5-difluorophenyl)methyl]piperidine fumarate;
Z-1-(4-fluorophenyl)-4-[4-(phenylmethyl)-1-piperidinyl]cyclohexanol;
Z-1-(4-fluorophenyl)-4-[4-[(3-methoxyphenyl)methyl]-1-piperidinyl]cyclohexanol;
Z-1-(4-fluorophenyl)-4-[4-[(2,5-difluorophenyl)methyl]-1-piperidinyl]cyclohexanol;
Z-1-(1,3-benzodioxol-5-yl)-4-[4-[(2-bromophenyl)methyl]-1-piperazinyl]cyclohexanol;

Z-1-(1,3-benzodioxol-5-yl)-4-[4-(diphenylmethyl)-1-piperazinyl]cyclohexanol;

Z-1-(1,3-benzodioxol-5-yl)-4-[4-(1-phenylethyl)-1-piperazinyl]cyclohexanol;

Z-1-[4-(4-fluorophenyl)-4-methoxy-1-cyclohexyl]-4-[(3-methoxyphenyl)methyl]piperazine;

Z-1-[4-(4-fluorophenyl)-4-methoxy-1-cyclohexyl]-4-[(3-methoxyphenyl)methyl]piperazine; and the like.

Another aspect of the present invention provides a method for treating a mammal, preferably a human being, afflicted with anxiety or panic disorders which comprises administering systematically to said mammal a therapeutically effective amount of a compound of Formula I or a pharmaceutically acceptable acid addition salt thereof.

The dosage and dosage regimen must in each case be carefully adjusted, utilizing sound professional judgement and considering such factors as the age, weight and condition of the recipient, the route of administration and the nature and gravity of the illness. Generally, however, the daily dose will be from about 0.01 to about 10 mg/kg, preferably 0.1 to 2 mg/kg, when administered parenterally and from about 1 to 50 mg/kg, when administered orally. In some instances a sufficient therapeutic effect can be obtained at lower doses while in others, greater doses will be required. Systemic administration refers to oral, rectal, transnasal, transdermal, and parenteral (i.e. intramuscular, intravenous, and subcutaneous). Generally it will be found that when a compound is administered orally, a greater quantity of the active agent is required to produce the same effect as a similar quantity given parenterally. In accordance with good clinical practice, it is preferred to administer the present compounds at a concentration level that will produce effective anxiolytic effects without causing any harmful or untoward side effects.

The compounds of the present invention may be administered for anxiolytic purposes either as individual therapeutic agents or as mixtures with other therapeutic agents. Therapeutically, they are generally given as pharmaceutical compositions comprised of an anxiolytic amount of a compound of Formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The compounds of the invention are also useful, in the dosages referred to above, in the prophylactic treatment of migraine (i.e., for the prevention of migraine headaches). The nature of the pharmaceutical composition employed will, of course, depend on the desired route of administration. For example, oral compositions may be in the form of tablets or capsules and may contain conventional excipients such as binding agents (e.g. starch) and wetting agents (e.g. sodium lauryl sulfate). Solutions or suspensions of a Formula I compound with conventional pharmaceutical vehicles are employed for parenteral compositions such as aqueous solution for intravenous injection or an oily suspension for intramuscular injection.

Compounds of Formula I can be prepared via processes set out below:

Scheme A: Synthesis of Compounds of Formula I from Intermediates, II and III.

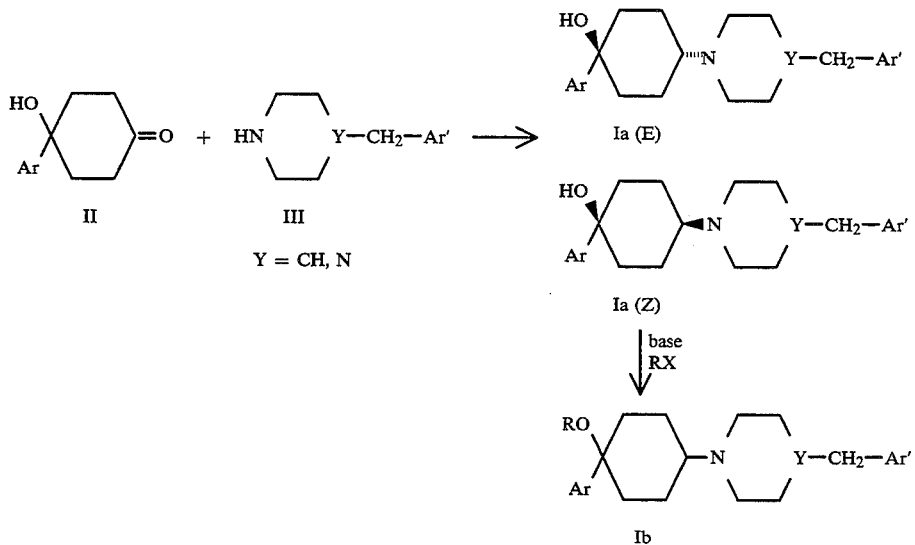

Compounds of Formula I are most conveniently synthesized by the coupling (Scheme A) of intermediates II and III under reductive alkylation conditions such as, titanium isopropoxide/NaBH$_4$, sodium cyanoborohydride, sodium triacetoxyborohydride and the like. Some of these methods give the products, Ia, as mixtures of the E (trans) and Z (cis) isomers which can be separated by chromatography, recrystallization, or other standard purification techniques. Other preferred methods, such as those employing titanium isopropoxide/NaBH$_4$, give Ia almost exclusively as the Z (cis) isomer.

The cyclohexanols, Ia, are further reacted with an alkylating agent and an appropriate base in a suitable solvent such as tetrahydrofuran, diethyl ether, dimethylformamide, dimethylacetamide, dimethyl sulfoxide, dioxane, dimethoxyethane, ethylene glycol dimethyl ether and the like, to give the ether derivatives, Ib. Appropriate bases for this reaction include, but are not limited to, sodium hydride, potassium hydride, calcium hydride, lithium hydride, sodium carbonate, potassium carbonate, sodium hydroxide, potassium hydroxide, calcium hydroxide, butyl lithium, methyl lithium, phenyl lithium and the like. Alkylating agents include, but are not limited to, methyl iodide, ethyl iodide, dimethyl sulfate, diethyl sulfate, propyl iodide, propyl bromide, methyl trifluoromethanesulfonate, ethyl trifluoro-methanesulfonate, methyl trifluoroacetate, ethyl trifluoroacetate, and the like.

Other methods known to those skilled in the art may also be used.

the ketals, IV. These reactions are generally carried out in solvents such as tetrahydrofuran, diethyl ether, dimethoxyethane, dioxane, ethylene glycol dimethylether and the like, at temperatures ranging from about −80° C. to about 30° C. The ketals, IV, are converted to the ketones, II, under acidic conditions such as, acetone/HCl, THF/HCl, acetone/H$_2$SO$_4$, THF/H$_2$SO$_4$, dioxane/HCl, and the like. Acids suitable for this hy- Scheme B: Preparation of Intermediates, II.

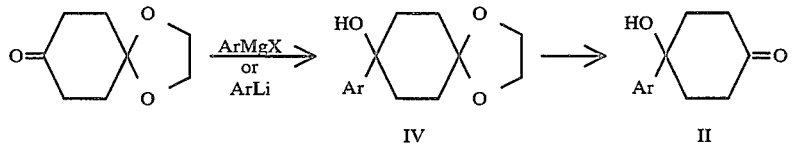

The ketone intermediates, II, are prepared (Scheme B) by reaction of cyclohexan-1,4-dione monoethyleneketal with organometallic reagents, such as Grignard reagents, aryl lithium reagents, and the like, to furnish drolysis include, but are not limited to, hydrochloric, sulfuric, acetic, phosphoric, paratoluenesulfonic, methanesulfonic, benzoic and the like.

Scheme C: Preparation of Intermediates, III.

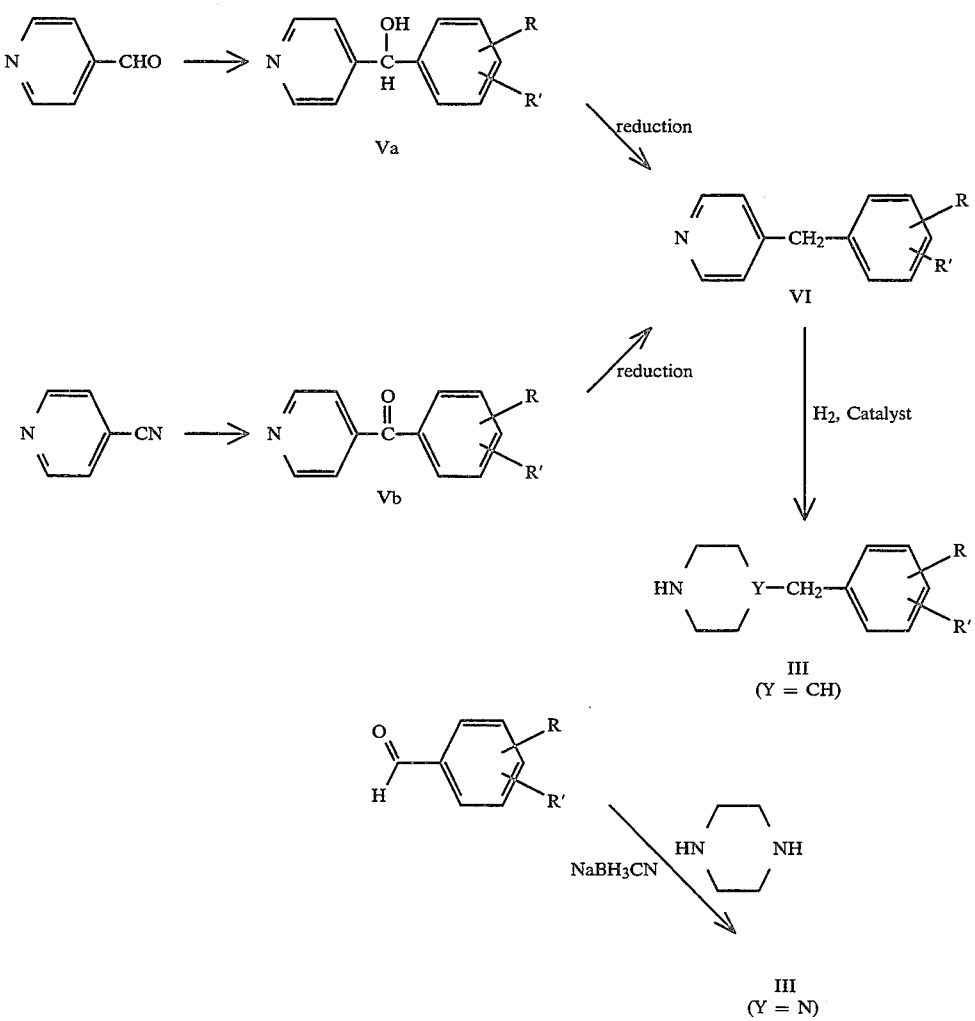

Scheme C: Preparation of Intermediates, III.

-continued

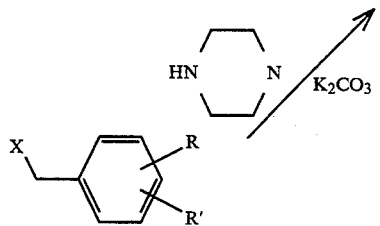

The intermediates, III (Y=CH), are prepared by the routes shown in Scheme C. Reaction of either pyridine-4-aldehyde or 4-cyanopyridine with appropriate organo-metallic reagents, such as Grignard reagents, aryl lithium reagents and the like, furnish the intermediates, Va and Vb. These organometallic reactions are generally carried out as described under Scheme B. The intermediates, Va and Vb, are reduced to the same arylmethylpyridine, VI, under catalytic reduction conditions using catalysts such as palladium on carbon, and the like, and sources of hydrogen such as hydrogen gas, ammonium formate, or hydrazine, and the like. Further reduction of VI, generally under acidic conditions using a catalyst such as platinum oxide, and the like, provides the desired intermediates, III (Y=CH).

The intermediates, III (Y=N), are prepared by reductively coupling an appropriately-substituted aryl aldehyde with piperazine, or a mono-protected piperazine under the usual conditions as described in Scheme A.

Also, intermediates, III (Y=CH), can be prepared by alkylation of piperazine, or a mono-protected piperazine, with an appropriately-substituted arylmethyl halide under standard conditions known to those skilled in the art. Appropriate reagents include arylmethyl halides, arylmethyl para-toluene-sulfonates, arylmethyl methane-sulfonates, and the like. Appropriate bases include potassium carbonate, sodium carbonate, potassium bicarbonate, sodium bicarbonate, triethylamine, tripropyl-amine tributylamine, pyridine, and the like. Suitable solvents include acetonitrile, tetrahydrofuran, dimethoxyethane, dioxane, acetone, dichloroethane, dimethyl-formamide, dimethylacetamide, dimethyl sulfoxide, and the like. Suitable protecting groups for piperazine include, but are not limited to, methylcarbamate, ethylcarbamate, t-butyl-carbamate, acetyl, formyl, propionyl, methanesulfonyl, p-toluenesulfonyl, and the like. The protecting groups can be subsequently removed by the usual methods known to those skilled in the art.

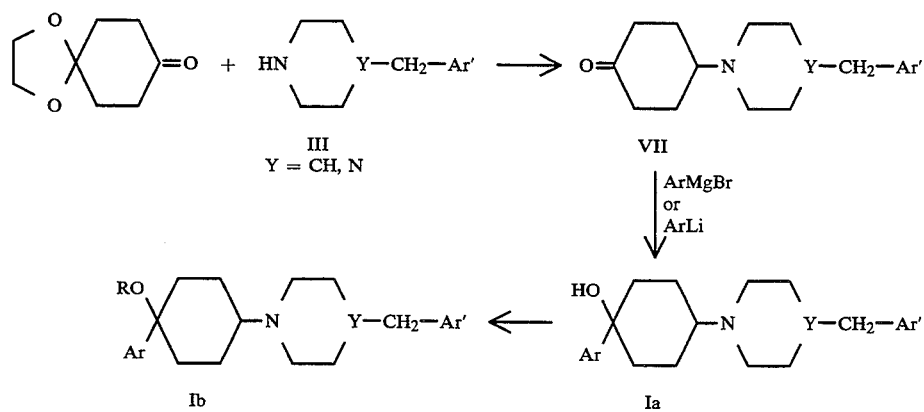

The compounds, I, are alternatively synthesized (Scheme D) by condensation of cyclohexan-1,4-dione mono-ethylene ketal with intermediate III under reductive alkylation conditions, such as described under Scheme A. Deprotection of the ketals under acidic conditions gives the ketones, VII. Subsequent addition of organo-metallic reagents, such as aryl Grignard reagents or aryl lithium reagents and the like, to the ketones, VII, gives the cyclohexanols, Ia, which are generally obtained as mixtures of the E (trans) and Z (cis) isomers that may be separated as described in Scheme A. The cyclohexanols, Ia, are then converted to the ether derivatives, Ib, as described in Scheme A.

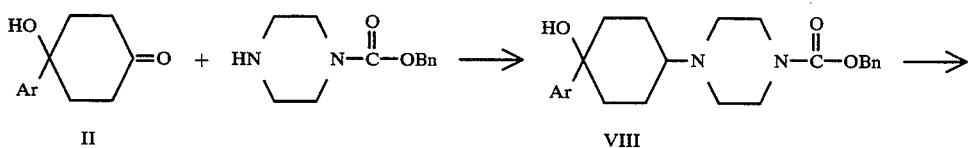

Scheme E: Alternate Synthesis Of Compounds, I, Where Y = N.

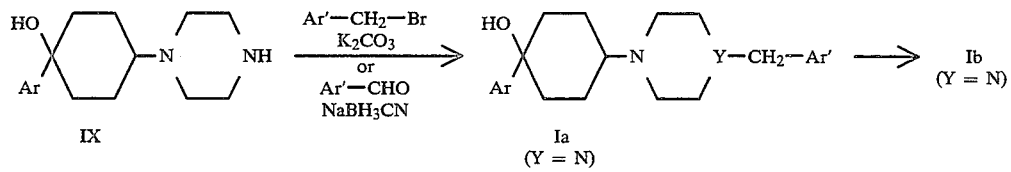

The compounds, I (Y=N), are alternatively synthesized by the route shown in Scheme E. The ketone intermediates, II, are reductively coupled with a mono-protected piperazine, such as carbobenzyloxypiperazine, under the usual conditions as described in Scheme A above to provide the intermediate, VIII. Other suitable protecting groups for piperazine include, but are not limited to, methylcarbamate, ethylcarbamate, t-butylcarbamate, acetyl, formyl, propionyl, methanesulfonyl, p-toluenesulfonyl, benzyl, appropriately substituted benzyl and the like. The intermediates, VIII, are generally obtained as mixtures of the E (trans) and Z (cis) isomers which can be separated as described in Scheme A. The intermediates, VIII, are deprotected to give the intermediates, IX, by the usual methods known to those skilled in the art. The compounds, IX, are then alkylated using standard methods described in Scheme C above to give compounds, Ia (Y=N).

Table I shows compounds of Formula I that were prepared by the methods described above. The compounds listed in the table conform to structure 1 (Z) or 1 (E):

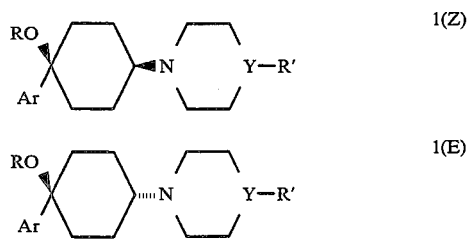

TABLE 1

| Example | Ar | R | Y | R' | E/Z | Yield | M.P. (°C.) |
|---|---|---|---|---|---|---|---|
| 15 | benzodioxole | H | CH | —CH$_2$—Ph | Z | 34.5% | 187–190.5 |
| 16 | MeO-phenyl | H | CH | —CH$_2$—Ph | Z | 22% | 177–179 |
| 17 | benzodioxole | H | N | —CH$_2$—Ph | Z | 22% | 164–168 |
| 18 | MeO-phenyl | H | N | —CH$_2$—Ph | Z | 50% | 179–180 |
| 19 | benzodioxole | Me | N | —CH$_2$—Ph | Z | 5% | 108–109 |
| 20-Z | benzodioxane | H | N | —CH$_2$—Ph | Z | 24% | 178–179 |
| 20-E | benzodioxane | H | N | —CH$_2$—Ph | E | 3.4% | 126–128 |

TABLE 1-continued
| Example | Ar | R | Y | R' | E/Z | Yield | M.P. (°C.) |
|---|---|---|---|---|---|---|---|
| 21 | 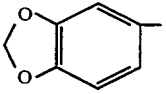 | H | N | —CH$_2$—C$_6$H$_4$—OMe (3-OMe) | Z | 60% | 166–167 |
| 22 | 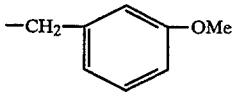 | H | N | —CH$_2$—C$_6$H$_4$—F (3-F) | Z | 74% | 159–160 |
| 23 | 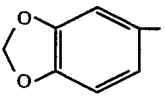 | H | N | —CH$_2$—C$_6$H$_4$—F (2-F) | Z | 73% | 160–161 |
| 24 | 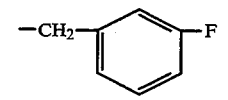 | H | N | —CH$_2$—C$_6$H$_4$—Me (2-Me) | Z | 82% | 168–170 |
| 25 | 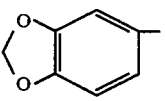 | H | N | —CH$_2$—C$_6$H$_4$—NO$_2$ (2-NO$_2$) | Z | 73% | 200–201 |
| 26 | 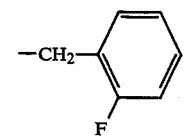 | H | N | —CH$_2$-(2-thienyl) | Z | 49% | 161–163 |
| 27 | 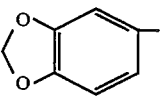 | H | N | —CH$_2$—C$_6$H$_4$—Cl (2-Cl) | Z | 63% | 174–175 |
| 28 | 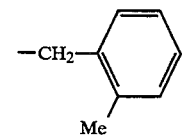 | H | N | —CH$_2$—C$_6$H$_3$—Cl$_2$ (2,4-Cl$_2$) | Z | 65% | 158–159 |
| 29 | 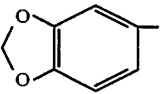 | H | N | —CH$_2$—C$_6$H$_3$—F$_2$ (2,5-F$_2$) | Z | 46% | 154–156 |
| 30 | 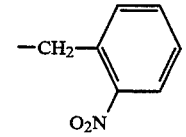 | H | N | —CH$_2$—C$_6$H$_3$—F$_2$ (2,3-F$_2$) | Z | 89% | 159–160 |

TABLE 1-continued
| Example | Ar | R | Y | R' | E/Z | Yield | M.P. (°C.) |
|---|---|---|---|---|---|---|---|
| 31 | 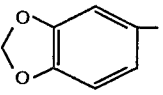 | H | N | 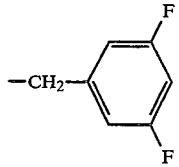 | Z | 39% | 160–161 |
| 32 | 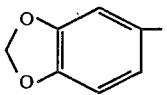 | H | N | 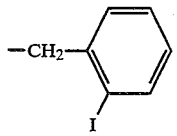 | Z | 67% | 168–171 |
| 33 | 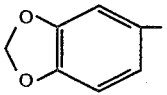 | H | N | 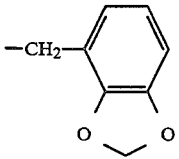 | Z | 83% | 162–163 |
| 34 |  | H | N | 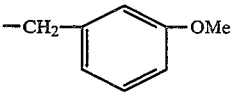 | Z | 63% | 162–163 |
| 35 | 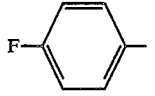 | H | N | 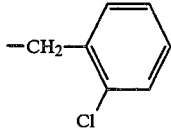 | Z | 80% | 164–165 |
| 36 | 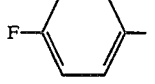 | H | N | 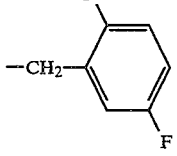 | Z | 84% | 149–151 |
| 37 | 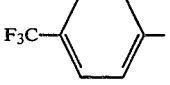 | H | N | 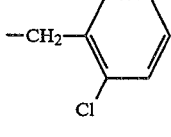 | Z | 45% | 161–162 |
| 38 | 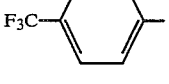 | H | N | 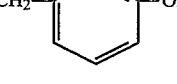 | Z | 46% | 131–132 |
| 39 | 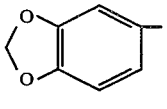 | H | N | 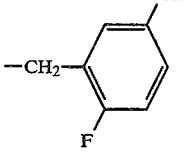 | Z | 16% | 136–137 |
| 40 | 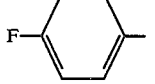 | H | N | 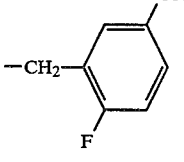 | Z | 21% | 159–161 |

TABLE 1-continued

| Example | Ar | R | Y | R' | E/Z | Yield | M.P. (°C.) |
|---|---|---|---|---|---|---|---|
| 41 | 2,3-dihydro-1,4-benzodioxin-6-yl | H | CH | —CH₂—C₆H₄—OMe (3-OMe) | Z | 5% | 183–185 |
| 42 | 1,3-benzodioxol-5-yl | H | CH | —CH₂—C₆H₄—OMe (3-OMe) | Z | 5% | 164–165 |
| 43 | 1,3-benzodioxol-5-yl | H | CH | —CH₂—C₆H₃(2-F)(5-F) | Z | 39% | 167–168 |
| 44 | 1,3-benzodioxol-5-yl | Me | CH | —CH₂—C₆H₄—OMe (3-OMe) | Z | 78% | 89–90 |
| 45 | 2,3-dihydro-1,4-benzodioxin-6-yl | Me | CH | —CH₂—C₆H₄—OMe (3-OMe) | Z | 17% | 165–170 (fumarate) |
| 46 | 1,3-benzodioxol-5-yl | Me | CH | —CH₂—C₆H₃(2-F)(5-F) | Z | 39% | 189–190 (fumarate) |
| 47 | 4-F—C₆H₄— | H | CH | —CH₂—Ph | Z | 44% | 160–161 |
| 48 | 4-F—C₆H₄— | H | CH | —CH₂—C₆H₄—OMe (3-OMe) | Z | 13% | 169–170 |
| 49 | 4-F—C₆H₄— | H | CH | —CH₂—C₆H₃(2-F)(5-F) | Z | 62% | 162–163 |
| 50 | 1,3-benzodioxol-5-yl | H | N | —CH₂—C₆H₄—Br (2-Br) | Z | 85% | 169–170 |
| 51 | 1,3-benzodioxol-5-yl | H | N | —CHPh₂ | Z | 88% | 210–211 |

TABLE 1-continued

| Example | Ar | R | Y | R' | E/Z | Yield | M.P. (°C.) |
|---|---|---|---|---|---|---|---|
| 52 | benzo[1,3]dioxol-5-yl | H | N | −CH(Me)−phenyl | Z | 90% | 177–178 |
| 53 | 4-F-phenyl | Me | N | −CH$_2$−(phenyl-OMe) | Z | 38% | 92–93 |
| 54 | 4-F-phenyl | Me | N | −CH$_2$−(2-Cl-phenyl) | Z | 44% | 66–67 |

EXAMPLES

The compounds which constitute this invention, their methods of preparation and their biological actions will be better appreciated after consideration of the following examples, which are given for the purpose of illustration only and are not be construed as limiting the invention. In the following examples, temperatures are expressed in degrees Celsius and melting points are uncorrected. Unless stated otherwise, all percentages given herein are weight percentages based on total composition weight.

The following examples describe in detail the preparation of compounds of Formula I, as well as synthetic intermediates in each process. It will be apparent to those skilled in the art that modifications, both of materials and methods, will allow preparation of other compounds disclosed herein.

A. Preparation Of Synthetic Intermediate Compounds

The following are summaries of the general procedures for making Intermediates of Formulas II and III.

A.1. General Procedures for Making Intermediates of Formula II

The ketone intermediates II can be made using Scheme B in which the cyclohexan-1,4-dione monoethylene ketal is reacted with Grignard or aryl lithium reagents to furnish ketals IV using suitable solvents and temperatures. The ketals IV are converted to ketones II using suitable acidic conditions.

A. 2. General Procedures for Making Intermediates of Formula III

1. Y=CH

When Y=CH, intermediates III can be made via the steps shown in Scheme C. Reactions of the starting pyridine-4-aldehyde or 4-cyanopyridine with, e.g., Grignard reagents or aryl lithium reagents, yields intermediates Va and Vb. The reactions using organometallics generally conform to Scheme B.

The intermediates Va and Vb are reduced to arylmethylpyridine VI under catalytic reduction conditions. Further reaction of VI, usually under acidic conditions with a catalyst, yields the desired intermediates III (Y=CH).

Also, when Y=CH, intermediates III can be made via the alkylation of piperazine or a mono-protected piperazine with an appropriate aryl methyl halide.

2. Y=N

When Y=N, intermediates III are produced by reductively coupling an appropriate aryl aldehyde with either piperazine or a mono-protected piperazine under the conditions set out in Scheme A.

Some representative procedures for preparation of synthetic intermediate compounds utilized above are given herein below. Most starting materials and certain intermediates are either commercially available or procedures for their synthesis are readily available in the chemical literature, allowing their full utilization by one skilled in the art of organic synthetic chemistry.

EXAMPLE 1

4-[4-(Phenylmethyl)-1-piperidinyl]cyclohexanone

Titanium(IV) isopropoxide (16.5 ml) was added to a mixture of 4-benzylpiperidine (8.76 g, 50 mmole) and 1,4-cyclohexanedione monoethylene ketal (7.81 g, 50 mmole) and gently heated. After stirring for 18 hr, the yellow oil was diluted with ethanol (100 ml) and NaBH$_4$ (2 g) was added. The mixture was stirred for 4 hr and water (10 ml) was added to precipitate the TiO$_2$. The mixture was filtered and filtrate was concentrated in vacuo to give 15.87 g (100%) of the crude ketal intermediate as a tan solid. This intermediate was stirred in a mixture of THF (75 ml) and 50% H$_2$SO$_4$ (75 ml) for 20 hr. The acid was neutralized with NaOH (50%) and Na$_2$CO$_3$ with ice bath cooling. The ketone product was extracted with ether and concentrated in vacuo. This yellow oil was Kügelrohr distilled to give a colorless oil that solidified upon standing to give 8.30 g (61.3%) of the ketone as colorless crystals.

EXAMPLE 2

4-[4-(Phenylmethyl)-1-piperazinyl]cyclohexanone

Titanium(IV) isopropoxide (74 ml) was added to a mixture of 1-benzylpiperazine (35.2 g, 200 mmole) and 1,4-cyclohexanedione monoethylene ketal (31.2 g, 200 mmole) and stirred until no ketone absorption was observed in the IR spectrum. The yellow oil was diluted with ethanol (200 ml) and NaBH$_4$ (7.6 g, 200 mmole) was added. The mixture was stirred for 16 hr and water (37 ml) was added to precipitate the TiO$_2$. The mixture was filtered and filtrate was concentrated in vacuo. The residue was dissolved in ether and the solution was washed with 1N HCl. The acid washes were basified with $K_2CO_3$, and the basic mixture extracted with methylene chloride. The extracts were dried over $K_2CO_3$ and concentrated in vacuo to give 56.5 g of ketal product, which was stirred in a mixture of THF (300 ml) and 50% $H_2SO_4$ (300 ml) for 2 hr. The solution was diluted with water (500 ml) and carefully basified with $K_2CO_3$. The basic mixture was extracted with ether and the extracts dried over sodium sulfate. Concentration in vacuo of the extract, followed by recrystallization from isopropyl ether, gave the product (41 g, 71%, mp: 83°–85° C.)

EXAMPLE 3

8-(1,3-Benzodioxol-5-yl)-1,4-dioxaspiro[4.5]decan-8-ol

A solution of 1,4-cyclohexanedione monoethylene ketal (31.2 g, 0.2 mole) in 100 ml dry THF was added to a −60° C. solution of the Grignard reagent prepared from magnesium metal (7.2 g, 0.3 mole) and 5-bromo-1,3-benzodioxole (60.3 g, 0.3 mole). The mixture was allowed to warm to 25° C. and quenched with saturated $NH_4Cl$ and extracted with ether. The extracts were dried with $Na_2SO_4$ and the solvent removed in vacuo. The residue was crystallized from isopropyl ether to give the product (47.5 g, 85%, m.p: 103°–104° C.).

EXAMPLE 4

4-(1,3-benzodioxol-5-yl)-4-hydroxycyclohexanone

A solution of 8-(1,3-benzodioxol-5-yl)-1,4-dioxas-piro[4.5]decan-8-ol (5 g, 18 mmole) in 75 ml acetone, 1 ml 12N HCl, and 50 ml water, was stirred for 2 hr. After dilution with an additional 50 ml water the solid was collected to give the product (4.0 g, 95%, mp: 166°–168° C.).

EXAMPLE 5

Phenylmethyl Z-4-[4-(1,3-benzodioxol-5-yl)-4-hydroxy-cyclohexyl]-1-piperazinecarboxylate A mixture of phenylmethyl 1-piperazinecarboxylate (5.65 g, 25.7 mmole), titanium(IV) isopropoxide (17 ml, 50 mmole), and 4-(1,3-benzodioxol-5-yl)-4-hydroxycyclohexanone (6.0 g, 25.7 mmole) was stirred for 18 hr. The mixture was dissolved in 50 ml ethanol and sodium borohydride (1.0 g, 25.7 mmole) was added. After stirring for 16 hr the mixture was quenched with 15% sodium hydroxide solution (6 ml). The mixture was filtered and the filtrate concentrated in vacuo. The residue was acidified with 1N HCl to give a solid. The solid was collected and suspended in water. The mixture was basified with sodium hydroxide and extracted with methylene chloride. The extracts were dried with $Na_2SO_4$ and concentrated in vacuo. The residue was crystallized from isopropyl ether to give the product (2.4 g, 22%, mp: 122°–124° C.). Calc'd for $C_{25}H_{30}N_2O_5 \cdot 0.5H_2O$: C, 67.10%; H, 6.99%; N, 6.26%. Found: C, 67.18%; H, 6.80%; N, 6.26%.

EXAMPLE 6

Z-1-(1,3-Benzodioxol-5-yl)-4-(1-piperazinyl)cyclohexanol

A mixture of phenylmethyl Z-4-[4-(1,3-benzodioxol-5-yl)-4-hydroxycyclohexyl]-1-piperazine-carboxylate (0.44 g, 1 mmole) and 10% palladium on charcoal (0.1 g) was hydrogenated for 1 hr. The catalyst was filtered off and the filtrate concentrated in vacuo. The residue was crystallized from isopropyl acetate to give the product (0.30 g, 93.5%, mp: 198°–199° C.). Calc'd for $C_{17}H_{24}N_2O_3$: C, 65.16%; H, 8.05%; N, 8.94%. Found: C, 65.27%; H, 7.69%; N, 8.83%.

EXAMPLE 7

8-(4-Fluorophenyl)-1,4-dioxaspiro[4.5]decan-8-ol

This compound was prepared from 1,4-cyclohexanedione monoethylene ketal (6.24 g, 40 mmole) and 4-fluorophenyl magnesium bromide (60 mmole) in a manner similar to example 3. The crude product was crystallized from hexane to give the product (8.9 g, 88%).

EXAMPLE 8

8-[4(-Trifluoromethyl)phenyl]-1,4-dioxaspiro[4.5]decan-8-ol

This compound was prepared from 1,4-cyclohexanedione monoethylene ketal (10.9 g, 70 mmole) and the Grignard reagent prepared from 4-bromobenzotrifluoride (25.0 g, 110 mmole) and magnesium (2.7 g, 110 mmole) in a manner similar to example 3. The crude product was crystallized from petroleum ether to give the product (20 g, 94.8% ). Calc'd. for $C_{15}H_{17}F_3O_3$: C, 59.60%; H, 5.67%. Found: C, 59.77%; H, 5.62%.

EXAMPLE 9

4-(4-Fluorophenyl)-4-hydroxycyclohexanone

This compound was prepared from 8-(4-fluorophenyl)-1,4-dioxaspiro[4.5]decan-8-ol (2.5 g, 10 mmole) in a manner similar to example 4. The crude material was crystallized from isopropyl ether to give the product (2.0 g, 95%, mp: 118°–119° C.). Calc'd. for $C_{12}H_{13}FO_2$: C, 69.22%; H, 6.30%. Found: C, 69.32%; H, 6.34%.

EXAMPLE 10

4-[4-(Trifluoromethyl)phenyl]-4-hydroxycyclohexanone

This compound was prepared from 8-[4(-trifluoromethyl)-phenyl]-1,4-dioxaspiro[4.5]decan-8-ol (10 g, 33 mmole) in a manner similar to example 4. The crude material was crystallized from isopropyl ether to give the product (7.5 g, 90.4% ). Calc'd. for $C_{13}H_{13}F_3O_2$: C, 60.47%; H, 5.71%. Found: C, 60.63%; H, 4.99%.

EXAMPLE 11

4-(3-Methoxybenzyl)piperidine

Step 1

A solution of 4-cyanopyridine in THF was added to the Grignard reagent prepared from 3-bromoanisole (37.4 g, 200 mmole) and magnesium (4.8 g, 200 mmole) in THF (400 ml) at −78° C. The solution was allowed to warm to 25° C. and quenched with ammonium chloride solution. The organic layer was separated and washed with water and 3N hydrochloric acid. The acid washes were stirred for 0.5 hr and neutralized with 50% sodium hydroxide. The basic mixture was extracted with ether. The extracts were dried and concentrated in vacuo. The crude material was crystallized from hexane to give 4-(3-methoxybenzoyl)pyridine (27 g, 63.3%).

Step 2

Ammonium formate (25 g) was added to a mixture of 4-(3-methoxybenzoyl)-pyridine (27 g, 127 mmole) and 10% palladium on charcoal (7 g) in acetic acid (250 ml).

The mixture was heated at reflux for 0.5 hr. The mixture was cooled and diluted with an equal volume of methylene chloride. The catalyst was removed and the solution concentrated in vacuo. The residue was dissolved in water and basified with sodium hydroxide. The mixture was extracted with ether. The extracts were dried and concentrated in vacuo to give the crude 4-(3-methoxybenzyl)pyridine (25 g, 98.8%) which was used without purification in the next step.

Step 3

A mixture of 4-(3-methoxybenzyl)pyridine (25 g, 126 mmole) and platinum oxide (2.4 g) in acetic acid (250 ml) was hydrogenated for 2 hr. The catalyst was removed and the solution concentrated in vacuo. The residue was dissolved in water and the solution basified with sodium hydroxide. The basic mixture was extracted with ether. The extracts were dried and concentrated in vacuo. The residue was vacuum distilled to give 4-(3-methoxy-benzyl)piperidine as an oil (22.6 g, 87.6%). A sample of the hydrochloride was prepared in ether (mp: 146°–147° C.). Calc'd. for $C_{13}H_{19}NO.HCl$: C, 64.59%; H, 8.34%; N, 5.80%. Found: C, 64.38%; H, 8.34%; N, 5.66%.

EXAMPLE 12

4-(2,5-Difluorobenzyl)piperidine

Step 1

Butyl lithium (70 ml of 2.22M solution, 155 mmole) was added to a solution of pentamethyldiethylenetriamine (23.3 ml, 155 mmole) in THF (250 ml) at −70° C. The solution was stirred for 5 min and 1,4-difluorobenzene (17.7 g, 155 mmole) in THF was added at −70° C. The solution was stirred for 2 hr during which time it was cooled to −75° C. and 4-cyanopyridine (15.6 g, 150 mmole) in THF was added at -75° C. The mixture was allowed to warm to 25° C. slowly and then quenched with ammonium chloride solution. The mixture was diluted with ether and the organic layer was separated. The organic layer was washed with water and 3N hydrochloric acid. The acid washes were stirred for 2 hr and basified with sodium hydroxide. The basic mixture was extracted with ether and the ether solution concentrated in vacuo. The crude product was purified by chromatography on silica eluting with ethyl acetate-hexane (20:1) to give 4-(2,5-difluorobenzoyl)pyridine (16.9 g, 51.5%).

Step 2

A mixture of 4-(2,5-difluorobenzoyl)pyridine (7.3 g, 33.3 mmole) and 10% palladium on charcoal in trifluoroacetic acid (50 ml) was 24 hydrogenated for 24 hr. The catalyst was removed and the solution concentrated in vacuo. The residue was dissolved in water and basified with sodium hydroxide. The basic mixture was extracted with ether and the ether extracts concentrated in vacuo. The crude 4-(2,5-difluorobenzyl)pyridine was used without purification in the next step.

Step 3

A mixture of platinum oxide (0.5 g) and 4-(2,5-difluorobenzyl)pyridine from above in acetic acid (100 ml) was hydrogenated for 3 hr. The catalyst was removed and the solution concentrated in vacuo. The residue was dissolved in water and the solution basified with sodium hydroxide. The basic mixture was extracted with ether and the extracts concentrated in vacuo. The crude oil was vacuum distilled to give the product (5.1 g, 72.9%, bp: 110° C.). A sample of the hydrochloride was prepared in ether (mp: 182°–183° C.). Calc'd. for $C_{12}H_{15}F_2N.HCl$: C, 58.19%; H, 6.52%; N, 5.66%. Found: C, 58.14%; H, 6.56%; N, 5.59%.

EXAMPLE 13

4-(2-Fluoro-5-methoxybenzyl)piperidine

Step 1.

Butyl lithium (47.5 ml of 2.22M solution, 105.6 mmole) was added slowly to a solution of pentamethyldiethylenetriamine (15 ml) and 4-fluoroanisole (12.61 g, 0.1 mole) in THF (150 ml) at −70° C. The solution was stirred for 2 hr at −75° C. and a solution of pyridine-4-aldehyde (9.55 ml, 0.1 mole) in THF was added at −75° C. The mixture was allowed to warm to 25° C. slowly and then quenched with ammonium chloride solution. The mixture was diluted with ethyl acetate and the organic layer was separated. The organic layer was washed with water and 3N hydrochloric acid. The acid washes were then basified with sodium hydroxide and extracted with ether and the ether solution concentrated in vacuo. The crude product was recrystallized from 80% ethanol to give (2-fluoro-5-methoxy-phenyl)-4-pyridylmethanol as a white powder (12.22 g+3.12 g second crop, 65.8% total yield).

Step 2

A mixture of (2-fluoro-5-methoxyphenyl)-4-pyridylmethanol and 10% palladium on charcoal in trifluoroacetic acid was hydrogenated similar to example 12, step 2. The catalyst was removed and the solution concentrated in vacuo. The residue was dissolved in water and basified with sodium hydroxide. The basic mixture was extracted with ether and the ether extracts concentrated in vacuo. The crude 4-(2-fluoro-5-methoxybenzyl)pyridine was used without purification in the next step.

Step 3

A mixture of 4-(2-fluoro-5-methoxybenzyl)pyridine (7.7 g, 35.5 mmole) and platinum oxide (0.7 g) in acetic acid (75 ml) was hydrogenated for 3 hr. The catalyst was removed and the acetic acid removed in vacuo. The residue was dissolved in water and the solution basified with sodium hydroxide. The basic mixture was extracted with ether. The extracts were dried and concentrated in vacuo. The residue was vacuum distilled to give the product (6 g, 75.9%).

EXAMPLE 14

4-(2-Fluoro-5-methoxybenzyl)piperazine

A solution of 2-formyl-4-methoxyfluorobenzene (5.0 g, 33 mmole, J. Organic Chem. 53 (14), p 3145 (1988)), piperazine (25.88 g, .3 mole), and sodium cyanoborohydride (3.08 g, 50 mmole) in ethanol (400 ml) was refluxed for 18 hr. The ethanol was removed in vacuo and the residue dissolved in water. The crude product was extracted from the aqueous mixture using methylene chloride. The methylene chloride extracts were concentrated in vacuo and the residue dissolved in 1N HCl. The acidic solution was extracted with methylene chloride and then made basic with sodium hydroxide. The product was extracted from the basic aqueous solution with methylene chloride. Concentrating the methylene chloride extracts in vacuo gave the product as a light yellow oil (3.63 g, 50%).

B. Preparation of Compounds of Formula I

The following are summaries of the general procedures for making componds of Formula I:

B.1. General Procedures for Making Compounds of Formula I via the Coupling of Intermediates II and III (Y=CH or N)

While other methods may be used, compounds of Formula I (wherein Y may be either CH or N) are generally made by coupling intermediates II and III (see Scheme A) using reductive alkylation. Some of these methods yield the cis and trans isomers of Ia, which isomers can be separated by known recovery techniques. Other methods, such as those using preferred reagents, give the cis isomer almost exclusively.

Cyclohexanols of Formula Ia are alkylated, using a base and a suitable solvent, to give ethers, Ib.

B.2. General Procedures for Making Compounds of Formula I using a Ketal and Intermediates II (Y=CH or N)

Scheme D depicts the synthesis of compounds of Formula I via the condensaton of cyclohexan-1,4-dione monoethylene ketal with intermediate III (Y may be CY or N) using reductive alkylation, as in Scheme A. Acidic deprotection of the ketals yields ketones, VII. Subsequent contacting of organometallics, e.g., Grignard or aryl lithium reagents, with the ketones, VII, gives cyclohexanols, Ia, as mixtures of cis and trans isomers. The isomers can be separated as described in Scheme A. The cyclohexanols, Ia, are converted to ethers Ib (Y=CH or N) as shown in Scheme A.

B.3. General Procedures for Making Compounds of Formula I (Y=N) Using Piperazines and Intermediates of Formula II Compounds of Formula I (Y=N) may be synthesized via Scheme E. A ketone intermediate, III, is reductively coupled with a mono-protected piperazine, under the conditions of Scheme A, to produce intermediate VIII (Scheme E) as a mixture of cis and trans isomers. The isomers can be separated as described in Scheme A. Intermediates VIII may be deprotected to yield intermediates IX by known methods. Compounds IX are alkylated using the method of, e.g., Scheme C to yield compounds Ia (Y=N).

EXAMPLE 15

Z-1-(1,3-Benzodioxol-5-yl)-4-[4-(phenylmethyl)-1-piperidinyl]cyclohexanol

A solution of 4-[4-(phenylmethyl)-1-piperidinyl]cyclohexanone (2.5 g, 9.23 mmole) in dry THF (20 ml) was added to the Grignard reagent prepared from magnesium metal (0.50 g. 20.5 mmole) and 5-bromo-1,3-benzodioxole (2.84 g, 14.1 mmole) in dry THF (25 ml). The reaction mixture was stirred for 1 hr before being quenched with saturated $NH_4Cl$ and extracted with ether. The ether extracts were dried with brine and concentrated in vacuo. The crude product was recrystallized twice from 20% ethyl acetate/c-hexane and dried in vacuo to give fluffy white crystals (1.25 g, 34.5 %, mp: 187°–190.5° C.). Calc'd for $C_{25}H_{31}NO_3$: C, 76.30%; H, 7.94%; N, 3.56%. Found: C, 76.30%; H, 8.11%; N, 3.76%.

EXAMPLE 16

Z-1-(4-Methoxyphenyl)-4-[4-(phenylmethyl)-1-piperidinyl]cyclohexanol

This compound was prepared in a Grignard reaction of 4-methoxyphenyl magnesium bromide (10 mmole) with 4-[4-(phenylmethyl)-1-piperidinyl]cyclo-hexanone (5.9 mmole) in a manner similar to the above procedure. The crude product was recrystallized twice from 10% ethyl acetate/c-hexane to give white crystalline flakes (0.50 g, 22 %, mp: 177°–179° C.). Calc'd. for $C_{25}H_{33}NO_2$: C, 79.11%; H, 8.77%; N, 3.69%. Found: C, 79.41%; H, 8.82%; N, 3.64%.

EXAMPLE 17

Z-1-(1,3-Benzodioxol-5-yl)-4-[4-(phenylmethyl)-1-piperazinyl]cyclohexanol

This compound was prepared in a Grignard reaction of 1,3-benzodioxol-5-yl magnesium bromide with 4-[4-(phenylmethyl)-1-piperazinyl]cyclohexanone in a manner similar to the above procedure. The crude material was recrystallized from isopropyl acetate to give the product in a 22% yield (mp: 167°–168° C.). Calc'd. for $C_{24}H_{30}N_2O_3$: C, 73.07%; H, 7.67%; N, 7.11%. Found: C, 73.05%; H, 7.67%; N, 7.09%.

EXAMPLE 18

Z-1-(4-Methoxyphenyl)-4-[4-(phenylmethyl)-1-piperazinyl]cyclohexanol

This compound was prepared in a Grignard reaction of 4-methoxyphenyl magnesium bromide with 4-[4-(phenylmethyl)1-piperazinyl]cyclohexanone in a manner similar to the above procedure. The crude material was recrystallized from isopropyl acetate to give the product in a 50% yield (mp: 179°–180° C.). Calc'd. for $C_{24}N_{32}N_2O_2$: C, 75.76%; H, 8.48%; N, 7.37% Found: C, 75.79%; H, 8.65%; N, 7.35%

EXAMPLE 19

Z-1-[4-(1,3-Benzodioxol-5-yl)-4-methoxycyclohexyl]-4-(phenylmethyl)piperazine

Sodium hydride (0.1 g, 2.5 mmole) was added to a solution of Z-1-(1,3-benzodioxol-5-yl)-4-[4-(phenylmethyl)-1-piperazinyl]cyclohexanol (1.0 g, 2.5 mmole) in dry THF (10 ml). After stirring for 1 hr the mixture was cooled to 5° C. and iodomethane (0.36 g, 2.5 mmole) added and the mixture allowed to stir for 18 hr. The mixture was diluted with water (25 ml) and extracted with $CH_2Cl_2$. The extracts were dried over $Na_2SO_4$ and concentrated in vacuo. The insoluble quaternary biproducts were removed by trituration with isopropanol. The isopropanol was then removed in vacuo. Starting material was removed by trituration with ether and the ether filtrate was chromatographed on silica using methanol/$CH_2Cl_2$ (1:50) to give a solid (50 mg, 5%, mp: 108°–109° C.) Calc'd. for $C_{25}H_{32}N_2O_3.0.5H_2O$: C, 71.91%; H, 7.97%; N, 6.71. Found: C, 71.71%; H, 7.50%; N, 6.62.

EXAMPLE 20

Z-1-(1,4-Benzodioxan-6-yl)-4-[4-(phenylmethyl)-1-piperazinyl]cyclohexanol, and

E-1-(1,4-Benzodioxan-6-yl)-4-[4-(phenylmethyl)-1-piperazinyl]cyclohexanol.

These compounds were prepared in a Grignard reaction of 1,4-benzodioxan-6-yl magnesium bromide and 4-[4-(phenylmethyl)1-piperazinyl]cyclohexanone in a manner similar to Example 15. The crude material was crystallized from diethyl ether to give the Z-isomer in a 24% yield (mp: 178°–179° C.). Calc'd. for $C_{25}H_{32}N_2O_3$ .0.05HO: C, 73.34%; H, 7.91%; N, 6.85. Found: C, 73.04%; H, 7.91%; N, 7.25.

The E-isomer was isolated from the mother liquors of the above compound by flash chromatography on silica gel eluting with methanol/methylene chloride (1:50) to give the E-isomer in 3.4% yield (m.p 126°–128° C.). Calc'd. for $C_{25}H_{32}N_2O_3.0.05\ H_2O$: C,73.34; H,7.91; N, 6.85. Found: C, 72.90; H, 7.91; N, 7.25.

EXAMPLE 21

Z-1-(1,3-Benzodioxol-5-yl)-4-[4-[(3-methoxyphenyl)-methyl]-1-piperazinyl]-cyclohexanol A mixture of 3-methoxybenzyl chloride (0.24 g, 1.5 mmole), Z-1-(1,3-benzodioxol-5-yl)-4-(1-piperazinyl)-cyclohexanol (0.45 g, 1.5 mmole) and excess potassium carbonate in acetonitrile (20 ml) was heated at reflux for 72 hr. The insolubles were removed, the solution concentrated in vacuo and the residue crystallized from isopropyl acetate to give the product (0.38 g, 60.3%, mp: 166°–167 ° C.). Calc'd. for $C_{25}H_{32}N_2O_4$: C, 70.73%; H, 7.60%; N, 6.60%. Found: C, 70.58%; H, 7.47%; N, 6.51%.

EXAMPLE 22

Z-1-(1,3-Benzodioxol-5-yl)-4-[4-[(3-fluorophenyl)methyl]-1piperazinyl]cyclohexanol This compound was prepared from Z-1-(1,3-benzodioxol-5-yl)-4-(1-piperazinyl)cyclohexanol and 3-fluorobenzyl chloride in a manner similar to example 21. The crude product was recrystallized from isopropyl acetate to give a white solid (74.1%, mp: 159°–160° C.). Calc'd. for $C_{24}H_{29}FN_2O_3.0.2H_2O$: C, 69.28%; H, 7.13%; N, 6.74%. Found: C, 68.97%; H, 6.96%; N, 6.58%.

EXAMPLE 23

Z-1-(1,3-Benzodioxol-5-yl)-4-[4-[(2-fluorophenyl)methyl]-1-piperazinyl]cyclohexanol This compound was prepared from Z-1-(1,3-benzodioxol-5-yl)-4-(1-piperazinyl)cyclohexanol and 2-fluorobenzyl chloride in a manner similar to example 21. The crude product was recrystallized from isopropyl acetate to give a white solid (72.5%, mp: 160°–161° C.). Calc'd. for $C_{24}H_{29}FN_2O_3$: C, 69.88%; H, 7.09%; N, 6.62%. Found: C, 69.79%; H, 7.08%; N, 6.62%

EXAMPLE 24

Z-1-(1,3-Benzodioxol-5-yl)-4-[4-[(2-methylphenyl)methyl]-1-piperazinyl]cyclohexanol This compound was prepared from Z-1-(1,3-benzodioxol-5-yl)-4(1-piperazinyl)cyclohexanol and 2-methylbenzyl chloride in a manner similar to example 21. The crude product was recrystallized from isopropyl acetate to give a white solid (82%, mp: 168°–170° C.). Calc'd. for: $C_{25}H_{32}N_2O_3\ .0.2H_2O$: C,72.86%; H, 7.93%; N, 6.80%; $H_2O$, 0.87%. Found: C, 73.02%; H, 7.91%; N, 6.67.%; $H_2O$, 0.46%

5 EXAMPLE 25

Z-1-(1,3-Benzodioxol-5-yl)-4-[4-[(2-nitrophenyl)methyl]-1-piperazinyl]cyclohexanol This compound was prepared from Z-1-(1,3-benzodioxol-5-yl)-4-(1-piperazinyl)cyclohexanol and 2-nitrobenzyl chloride in a manner similar to example 21. The crude product was recrystallized from isopropyl acetate to give a white solid (72.7%, mp: 200°–201° C.). Calc'd. For $C_{24}H_{29}N_3O_5$: C, 65.59%; H, 6.66%; N, 9.57%. Found: C, 65.51%; H, 6.69%; N, 9.45%.

EXAMPLE 26

Z-1-(1,3-Benzodioxol-5-yl)-4-[4-(2-thienylmethyl)-1-piperazinyl]cyclohexanol

A solution of Z-1-(1,3-benzodioxol-5-yl)-4-(1-piperazinyl)cyclohexanol (0.6 g, 2 mmole), thiophene-2-carboxaldehyde (0.22 g, 2 mmole) and sodium cyanoboro-hydride (0.12 g, 2 mmole) in ethanol (20 ml) was heated at reflux for 36 hr. Water (5 ml) was added to the solution and the ethanol removed in vacuo. The residue was extracted with methylene chloride. The extracts were dried with $Na_2SO_4$ and concentrated in vacuo. The crude product was recrystallized from isopropyl acetate to give a beige solid (0.39 g, 48.8%, mp: 161°–163° C.). Calc'd. for $C_{22}H_{28}N_2O_3S$: C, 65.97%; H, 7.05%; N, 6.99%. Found: C, 65.94%; H, 7.05%; N, 6.97%

EXAMPLE 27

Z-1-(1,3-Benzodioxol-5-yl)-4-[4-[(2-chlorophenyl)methyl]-1-piperazinyl]cyclohexanol This compound was prepared from Z-1-(1,3-benzodioxol-5-yl)-4-(1-piperazinyl)cyclohexanol and 2-chlorobenzaldehyde in a manner similar to example 26. The crude product was recrystallized from isopropyl acetate to give a white solid (62.5%, mp: 174°–175° C.). Calc'd. for $C_{24}H_{29}ClN_2O_3$: C, 67.21%; H, 6.82%; N, 6.54%. Found: C, 66.89%; H, 6.86%; N, 6.51%

EXAMPLE 28

Z-1-(1,3-Benzodioxol-5-yl)-4-[4-[(2,5-dichlorophenyl)-methyl]-1-piperazinyl]-cyclohexanol This compound was prepared from Z-1-(1,3-benzodioxol-5-yl)-4-(1-piperazinyl)cyclohexanol and 2,5-dichlorobenzyl chloride in a manner similar to example 21. The crude product was recrystallized from isopropyl ether to give a white solid (65.2%, mp: 158°–159° C.). Calc'd. For $C_{24}H_{28}Cl_2N_2O_3$: C, 62.20%; H, 6.09%; N, 6.05%. Found: 62.26%; H, 6.11%; N, 5.96%.

EXAMPLE 29

Z-1-(1,3-Benzodioxol-5-yl)-4-[4-[(2,5-difluorophenyl)-methyl]-1piperazinyl]-cyclohexanol This compound was prepared from Z-1-(1,3-benzodioxol-5-yl)-4-(1-piperazinyl)cyclohexanol and 2,5-difluorobenzyl bromide in a manner similar to example 21. The crude product was recrystallized from isopropyl acetate to give a white solid (46.0%, mp: 154°–156° C.). Calc'd. For $C_{24}H_{28}F_2N_2O_3.0.2H_2O$: C, 66.40%; H, 6.60%; N, 6.45%. Found: 66.39%; H, 6.50%; N, 6.46%.

EXAMPLE 30

Z-1-(1,3-Benzodioxol-5-yl)-4-[4-[(2,3-difluorophenyl)-methyl]-1-piperazinyl]-cyclohexanol This compound was prepared from Z-1-(1,3-benzodioxol-5-yl)-4-(1-piperazinyl)cyclohexanol and 2,3-difluorobenzyl bromide in a manner similar to example 21. The crude product was recrystallized from isopropyl acetate to give a white solid (88.5%, mp: 159°–160° C.). Calc'd. For $C_{24}H_{28}F_2N_2O_3.0.1H_2O$: C, 66.68%; H, 6.58%; N, 6.48%. Found: 66.46%; H, 6.51%; N, 6.28%.

EXAMPLE 31

Z-1-(1,3-Benzodioxol-5-yl)-4-[4-[(3,5-difluorophenyl)-methyl]-1-piperazinyl]-cyclohexanol This compound was prepared from Z-1-(1,3-benzodioxol-5-yl)-4-(1-piperazinyl)cyclohexanol and 3,5-difluorobenzyl bromide in a manner similar to example 21. The crude product was recrystallized from isopropyl acetate to give a white solid (38.6%, mp: 160°–161° C.). Calc'd. For $C_{24}H_{28}F_2N_2O_3.0.1H_2O$: C, 66.68%; H, 6.58%; N, 6.48%. Found: 66.46%; H, 6.51%; N, 6.23%.

EXAMPLE 32

Z-1-(1,3-Benzodioxol-5-yl)-4-[4-[(2-iodophenyl)methyl]-1-piperazinyl]cyclohexanol This compound was prepared from Z-1-(1,3-benzodioxol-5-yl)-4-(1-piperazinyl)cyclohexanol and 2-iodobenzyl bromide in a manner similar to example 21. The crude product was recrystallized from isopropyl acetate to give a white solid (67.3%, mp: 168°–171° C.). Calc'd. For $C_{24}H_{29}IN_2O_3$: C, 55.40%; H, 5.62%; N, 5.38%. Found: 55.76%; H, 5.55%; N, 5.37%.

EXAMPLE 33

Z-1-(1,3-Benzodioxol-5-yl)-4-[4-[(1,3-benzodioxo-4-yl)methyl]-1-piperazinyl]-cyclohexanol This compound was prepared from Z-1-(1,3-benzodioxol-5-yl)-4-(1-piperazinyl)cyclohexanol and 2,3-methyenedioxybenzyl chloride in a manner similar to example 21. The crude product was recrystallized from isopropyl acetate to give a white solid (83.3%, mp: 163°–164° C.). Calc'd. For $C_{25}H_{30}N_2O_5$: C, 68.47%; H, 6.90%; N, 6.39%. Found: 68.20%; H, 6.85%; N, 6.29%.

EXAMPLE 34

Z-1-(4-Fluorophenyl)-4-[4-[(3-methoxyphenyl)methyl]-1-piperazinyl]cyclohexanol

This compound was prepared from Z-1-(4-fluorophenyl)-4-(1-piperazinyl)-cyclohexanol and 3-methoxybenzyl chloride in a manner similar to example 21. The crude product was recrystallized from isopropyl acetate to give a white solid (62.5%, mp: 162°–163° C.). Calc'd. For $C_{24}H_{31}FN_2O_2.0.2H_2O$: C, 71.68%; H, 7.87%; N, 6.97%. Found: 71.57%; H, 7.82%; N, 6.91%.

EXAMPLE 35

Z-1-(4-Fluorophenyl)-4-[4-[(2-chlorophenyl)methyl]-1-piperazinyl]cyclohexanol

This compound was prepared from Z-1-(4-fluorophenyl)-4-(1-piperazinyl)-cyclohexanol and 2-chlorobenzyl chloride in a manner similar to example 21. The crude product was recrystallized from isopropyl acetate to give a white solid (80.2%, mp: 164°–165° C.). Calc'd. For $C_{23}H_{28}ClFN_2O$: C, 68.56%; H, 7.00%; N, 6.95%. Found: 68.28%; H, 6.92%; N, 6.86%.

EXAMPLE 36

Z-1-(4-Fluorophenyl)-4-[4-[(2,5-difluorophenyl)methyl]-1-piperazinyl]cyclohexanol This compound was prepared from Z-1-(4-fluorophenyl)-4-(1-piperazinyl)cyclohexanol and 2,5-difluorobenzyl bromide in a manner similar to example 21. The crude product was recrystallized from isopropyl acetate to give a white solid (84.3%, mp: 149°–151° C.). Calc'd. For $C_{23}H_{27}F_3N_2O.0.5H_2O$: C, 66.81%; H, 6.83%; N, 6.78%. Found: 66.46%; H, 6.50%; N, 6.64%.

EXAMPLE 37

Z-1-[(4-Trifluoromethyl)phenyl]-4-[4-[(2-chlorophenyl)methyl]-1-piperazinyl]-cyclohexanol This compound was prepared from Z-1-[(4-trifluoromethyl)phenyl]-4-(1-piperazinyl)cyclohexanol and 2-chlorbenzyl chloride in a manner similar to example 21. The crude product was recrystallized from isopropyl ether to give a beige solid (45.2%, mp: 161°–162° C.). Calc'd. For $C_{24}H_{28}ClF_3N_2O$: C, 63.64%; H, 6.23%; N, 6.19%. Found: 63.26%; H, 6.27%; N, 6.20%.

EXAMPLE 38

Z-1-[(4-Trifluoromethyl)phenyl]-4-[4-[(3-methoxyphenyl)methyl]-1-piperazinyl]-cyclohexanol This compound was prepared from 4-[4-(trifluoromethyl)phenyl]-4-hydroxy-cyclohexanone, titanium isopropoxide, sodium borohydride and (3-methoxybenzyl)-piperazine in a manner similar to example 5. The crude product was recrystallized from isopropyl ether to give a beige solid (46.4%, mp: 131°–132° C.). Calc'd. For $C_{25}H_{31}F_3N_2O_3.0.45H_2O$: C, 65.75%; H, 7.04%; N, 6.13%. Found: 65.45%; H, 6.58%; N, 6.66%.

EXAMPLE 39

Z-1-(1,3-Benzodioxol-5-yl)-4-[4-[(2-fluoro-5-methoxyphenyl) methyl]-1-piperazinyl]cyclohexanol This compound was prepared from 4-(1,3-benzodioxol-5-yl)-4-hydroxycyclohexanone, titanium isopropoxide, sodium borohydride and (2-fluoro-5-methoxy-benzyl)piperazine in a manner similar to example 5. The crude product was recrystallized from isopropyl ether to give a white solid (16.4%, mp: 136°–137° C.). Calc'd. For $C_{25}H_{31}FN_2O_4$: C, 67.85%; H, 7.06%; N, 6.33%. Found: 67.41%; H, 6.91%; N, 6.36%.

EXAMPLE 40

Z-1-(4-Fluorophenyl)-4-[4-[(2-fluoro-5-methoxyphenyl)methyl]-1-piperazinyl]cyclohexanol This compound was prepared from 4-(4-fluorophenyl)-4-hydroxycyclohexanone, titanium isopropoxide, sodium borohydride and (2-fluoro-5-methoxy-benzyl)piperazine in a manner similar to example 5. The crude product was recrystallized from isopropyl acetate to give a white solid (21.1%, mp: 159°–161° C.). Calc'd. For $C_{24}H_{30}F_2N_2O_2$: C, 69.21%; H, 7.26%; N, 6.73%. Found: 69.52%; H, 7.41%; N, 6.81%.

EXAMPLE 41

Z-1-(1,4-Benzodioxan-6-yl)-4-[4-[(3-methoxyphenyl)-methyl]-1-piperidinyl]cyclohexanol This compound was prepared from 4-(1,4-benzodioxan-6-yl)-4-hydroxy-cyclohexanone, titanium isopropoxide, sodium borohydride and 4-(3-methoxy-benzyl)-piperidine in a manner similar to example 5. The crude product was recrystallized from isopropyl acetate to give a white solid (5.0%, mp: 183°–185° C.). Calc'd. For $C_{27}H_{35}NO_4.0.5H_2O$: C, 72.61%; H, 8.13%; N, 3.14%. Found: 72.33%; H, 7.94%; N, 3.02%.

EXAMPLE 42

Z-1-(1,3-Benzodioxol-5-yl)-4-[4-[(3-methoxyphenyl)-methyl]-1-piperidinyl]cyclohexanol This compound was prepared from 4-(1,3-benzodioxol-5-yl)-4-hydroxycyclohexanone, titanium isopropoxide, sodium borohydride and 4-(3-methoxybenzyl)-piperidine in a manner similar to example 5. The crude product was recrystallized from isopropyl acetate to give a white solid (4.9%, mp: 164°–165° C.). Calc'd. For $C_{26}H_{33}NO_4$: C, 73.73%; H, 7.85%; N, 3.31%. Found: 73.45%; H, 7.88%; N, 3.20%.

EXAMPLE 43

Z-1-(1,3-Benzodioxol-5-yl)-4-[4-[(2,5-difluorophenyl)-methyl]-1-piperidinyl]cyclohexanol This compound was prepared from 4-(1,3-benzodioxol-5-yl)-4-hydroxycyclohexanone, titanium isopropoxide, sodium borohydride and 4-(2,5-difluorobenzyl)-piperidine in a manner similar to example 5. The crude product was recrystallized from isopropyl ether to give a white solid (38.5%, mp: 167°–168° C.). Calc'd. For C25H29F2NO3: C, 69.91%; H, 6.81%; N, 3.26%. Found: 69.82%; H, 6.71%; N, 3.24%.

EXAMPLE 44

Z-1-[4-(1,3-Benzodioxol-5-yl)-4-methoxy-1-cyclohexyl]-4-[(3-methoxyphenyl)methyl]-piperidine This compound was prepared from 4-(1,3-benzodioxol-5-yl)-4-methoxycyclohexanone, titanium isopropoxide, sodium borohydride and 4-(3-methoxybenzyl)-piperidine in a manner similar to example 5. The crude product was recrystallized from hexane to give a white solid (78%, mp: 89°–90° C.). Calc'd. For C27H35NO4: C, 74.11%; H, 8.06%; N, 3.20%. Found: 73.89%; H, 8.00%; N, 3.15%.

EXAMPLE 45

Z-1-[4-(1,4-Benzodioxan-6-yl)-4-methoxy-1-cyclohexyl]-4-[3-(methoxyphenyl)methyl]-piperidine fumarate This compound was prepared from 4-(1,4-benzodioxan-6-yl)-4-methoxycyclohexanone, titanium isopropoxide, sodium borohydride and 4-(3-methoxybenzyl)-piperidine in a manner similar to example 5. The crude product was converted to the fumarate salt in ethyl acetate-methanol to give a white solid (16.7%, mp: 165°–170° C.). Calc'd. For $C_{28}H_{37}NO_4 \cdot C_4H_4O_4$: C, 67.70%; H, 7.28%; N, 2.47%. Found: 67.29%; H, 7.10%; N, 2.46%.

EXAMPLE 46

Z-1-[4-(1,3-Benzodioxol-5-yl)-4-methoxy-1-cyclohexyl]-4-[(2,5-difluorophenyl)-methyl]piperidine fumarate This compound was prepared from 4-(1,3-benzodioxol-5-yl)-4-methoxycyclohexanone, titanium isopropoxide, sodium borohydride and 4-(2,5-difluorobenzyl)-piperidine in a manner similar to example 5. The crude material was converted to the fumarate salt in acetone to give a white solid (38.5%, mp: 189°–190° C.). Calc'd. For $C_{26}H_{31}F_2NO_3 \cdot C_4H_4O_4 \cdot 0.1H_2O$: C, 64.18%; H, 6.32%; N, 2.50%. Found: C, 63.93%; H, 6.27%; N, 2.53%.

EXAMPLE 47

Z-1-(4-Fluorophenyl)-4-[4-(phenylmethyl)-1-piperidinyl]cyclohexanol

This compound was prepared from 4-(4-fluorophenyl)-4-hydroxycyclohexanone, titanium isopropoxide, sodium borohydride and 4-benzylpiperidine in a manner similar to example 5. The crude product was recrystallized from isopropyl acetate to give a white solid (44.4%, mp: 160°–161° C.). Calc'd. For $C_{24}H_{30}FNO \cdot 0.2H_2O$: C, 77.67%; H, 8.26%; N, 3.78%. Found: 77.74%; H, 8.13%; N, 3.78%.

EXAMPLE 48

Z-1-(4-Fluorophenyl)-4-[4-[(3-methoxyphenyl)methyl]-1-piperidinyl]cyclohexanol

This compound was prepared from 4-(4-fluorophenyl)-4-hydroxycyclohexanone, titanium isopropoxide, sodium borohydride and 4-(3-methoxybenzyl)-piperidine in a manner similar to example 5. The crude product was recrystallized from isopropyl acetate to give a white solid (12.5%, mp: 169°–170° C.). Calc'd. For $C_{24}H_{32}FNO_2 \cdot 0.5H_2O$: C, 73.86%; H, 8.18%; N, 3.45%. Found: 73.93%; H, 7.93%; N, 3.44%.

EXAMPLE 49

Z-1-(4-Fluorophenyl)-4-[4-[(2,5-difluorophenyl)methyl]-1-piperidinyl]cyclohexanol This compound was prepared from 4-(4-fluorophenyl)-4-hydroxycyclohexanone, titanium isopropoxide, sodium borohydride and 4-(2,5-difluorobenzyl)-piperidine in a manner similar to example 5. The crude product was recrystallized from isopropyl ether to give a white solid (61.5%, mp: 162°–163° C.). Calc'd. For $C_{24}H_{28}F_3NO$: C, 71.44%; H, 7.00%; N, 3.47%. Found: 71.23%; H, 7.12%; N, 3.42%.

EXAMPLE 50

Z-1-(1,3-Benzodioxol-5-yl)-4-[4-[(2-bromophenyl)methyl]-1-piperazinyl]cyclohexanol This compound was prepared from Z-1-(1,3-benzodioxol-5-yl)-4-(1-piperazinyl)cyclohexanol and 2-bromobenzyl bromide in a manner similar to example 21. The crude product was recrystallized from isopropyl acetate to give a white solid (84.5%, mp: 169°–170° C.). Calc'd. For $C_{24}H_{29}BrN_2O_3$: C, 60.90%; H, 6.18%; N, 5.92%. Found: 61.26%; H, 6.25%; N, 5.82%.

EXAMPLE 51

Z-1-(1,3-Benzodioxol-5-yl)-4-[4-(diphenylmethyl)-1-piperazinyl]cyclohexanol

This compound was prepared from Z-1-(1,3-benzodioxol-5-yl)-4-(1-piperazinyl)cyclohexanol and chlorodiphenylmethane in a manner similar to example 21. The crude product was recrystallized from isopropyl acetate to give a white crystals (87.8%, mp: 210°–211° C.). Calc'd. For $C_{30}H_{34}N_2O_3 \cdot 0.3H_2O$: C, 75.70%; H, 7.33%; N, 5.89%. Found: 75.48%; H, 7.26%; N, 5.96%.

EXAMPLE 52

Z-1-(1,3-Benzodioxol-5-yl)-4-[4-(1-phenylethyl)-1-piperazinyl]cyclohexanol

This compound was prepared from Z-1-(1,3-benzodioxol-5-yl)-4-(1-piperazinyl)cyclohexanol, titanium isopropoxide, sodium borohydride and acetophenone in a manner similar to example 5. The crude product was recrystallized from isopropyl acetate to give a white solid (90%, mp: 177°–178° C.). Calc'd. For $C_{25}H_{32}N_2O_3 \cdot 0.3H_2O$: C, 72.86%; H, 7.93%; N, 6.80%. Found: 72.74%; H, 7.76%; N, 6.76%.

EXAMPLE 53

Z-1-[4-(4-Fluorophenyl)-4-methoxy-1-cyclohexyl]-4-[(3-methoxyphenyl)-methyl]piperazine Step 1

Sodium hydride (1.27 g, 31.7 mmole) was added to a solution of 8-(4-fluoro-phenyl)-1,4-dioxaspiro[4.5]decan-8-ol (8.0 g, 10 mmole) in THF (100 ml) and the mixture stirred for 16 hr and heated at reflux for 4 hr. The solution was cooled to 25° C. and iodomethane (6.75 g, 47.6 mmole) was added. The mixture was stirred for 112 hr and concentrated in vacuo. The residue was suspended in water and the mixture extracted with methylene chloride. The extracts were dried and concentrated in vacuo to give 8-(4-fluorophenyl)-1,4-dioxaspiro[4.5]decan-8-ol methyl ether (98.8%, mp: 52°–54° C.).

Step 2

A solution of 8-(4-fluorophenyl)-1,4-dioxaspiro[4.5]decan-8-ol methyl ether in acetone (200 ml) was stirred for 96 hr with p-toluenesulfonic acid (0.1 g) and the solution diluted with saturated $NaHCO_3$ solution. The mixture was concentrated in vacuo and the residue suspended in water. The mixture was extracted with ether and the ether extracts dried and concentrated in vacuo. The residue was crystallized from hexane to give 4-(4-fluoro-phenyl)-4-methoxycyclohexanone (94%, mp: 57°–59° C.).

Step 3

A mixture of 4-(4-fluorophenyl)-4-methoxycyclohexanone (2,2 g, 10 mmole), phenylmethyl 1-piperazinecarboxylate (2.2 g, 10 mmole), titanium(IV) isopropoxide (3.7 ml, 11 mmole) were mixed, reacted and reduced with sodium borohydride (0.4 g, 10 mmole) as in example 5. The crude product was purified by chromatography on silica eluting with methanol-methylene chloride (1:50) to give phenylmethyl [4-(4-fluorophenyl)-4-methoxy-1-cyclohexyl]-1-piperazinecarboxylate (35.7%, mp: 68°–69° C.).

Step 4

A mixture of phenylmethyl [4-(4-fluorophenyl)-4-methoxy-1-cyclohexyl]-1-piperazinecarboxylate (1.25 g, 2.9 mmole) and 10% palladium on charcoal (0.2 g) in methanol (50 ml) was hydrogenated for 2 hr. The catalyst was removed and the solution concentrated in vacuo. The material was crystallized from hexane to give 1-[4-(4-fluorophenyl)-4-methoxy-1-cyclohexyl]-piperazine (73.8%).

Step 5

A mixture of 1-[4-(4-fluorophenyl)-4-methoxy-1-cyclohexyl]piperazine (0.33 g, 1.1 mmole) and 3-methoxybenzyl bromide (0.18 g, 1.1 mmole) was reacted as in example 21. The crude material was crystallized from hexane to give the product (37.8%, mp: 92°–93° C.). Calc'd. For $C_{24}H_{33}FN_2O_2$: C, 72.79%; H, 8.07%; N, 6.80%. Found: 72.73%; H, 8.15%; N, 6.71%.

EXAMPLE 54

Z-1-[4-(4-Fluorophenyl)-4-methoxy-1-cyclohexyl]-4-[(2-chlorophenyl)-methyl]piperazine A mixture of 1-[4-(4-fluorophenyl)-4-methoxy-1-cyclohexyl]piperazine (0.33 g, 1.1 mmole) and 2-chlorobenzyl chloride (0.18 g, 1.1 mmole) was reacted as in example 21. The crude material was crystallized from hexane to give the product (44.4%, mp: 66°–67° C.). Calc'd. For $C_{24}H_{30}FN_2O$: C, 68.25%; H, 7.31%; N, 6.64%. Found: 68.07%; H, 7.18%; N, 6.50%.

Table 2 shows the in vitro receptor binding affinities of the compounds made in Examples 15 through 52.

TABLE 2

| IN VITRO RECEPTOR BINDING ACTIVITIES | | |
|---|---|---|
| EXAMPLE | $5\text{-HT}_{1A}$ (nM) | $D_2$ (nM) |
| 15 | 5.4 | >1000 |
| 16 | 15.6 | 2,710 |
| 17 | 20 | 1,710 |
| 18 | 46.5 | 1,830 |
| 19 | 14 | 1,350 |
| 20-Z | 9.9 | 15,200 |
| 20-E | 5.3 | — |
| 21 | 2.15 | 1,040 |
| 22 | 13.4 | — |
| 23 | 10.1 | 1,540 |
| 24 | 4.2 | 2,550 |
| 25 | 12.8 | 7,080 |
| 26 | 19.1 | — |
| 27 | 1.85 | — |
| 28 | 0.6 | — |
| 29 | 2.6 | — |
| 30 | 17.3 | — |
| 31 | 21.1 | — |
| 32 | 1.2 | — |
| 33 | 34.9 | — |
| 34 | 10.6 | — |
| 35 | 5.9 | — |
| 36 | 34.7 | — |
| 37 | 25.8 | — |
| 38 | 35.6 | — |
| 39 | 0.75 | — |
| 40 | 3.45 | — |
| 41 | 2.2 | — |
| 42 | 4.4 | — |
| 43 | 4.9 | — |
| 44 | 8.2 | 49,234 |
| 45 | 3.4 | — |
| 46 | 16.2 | — |
| 47 | 59.8 | — |
| 48 | 31.9 | — |
| 49 | 57.6 | — |
| 50 | 1.2 | — |
| 51 | 28.6 | — |
| 52 | 18.1 | — |

Table 3 shows the in vivo activity of selected compounds made in Examples 7 through 50 in the rat social interaction task.

TABLE 3

| IN VIVO ACTIVITY | |
|---|---|
| EXAMPLE | RAT SOCIAL INTERACTION TASK Active doses |
| 15 | 0.01–.1 mpk |
| 17 | 0.1–1.0 mpk |
| 18 | 0.1–1.0 mpk |
| 19 | 0.1 mpk |
| 20-Z | 0.001–0.01 mpk |
| 36 | 0.01–10 mpk |
| 44 | 0.001–0.01 mpk |
| 49 | 0.1 mpk |
| 50 | 0.01–0.1 mpk |

The compounds comprising the present invention are selective antagonists and partial agonists at the serotonergic $5\text{-HT}_{1A}$ receptor. Serotonergic pathways are implicated in a variety of psychiatric disorders such as anxiety and panic disorders, and it is known that antagonists of the $5\text{-HT}_{1A}$ receptor are clinically effective in the treatment of anxiety (see: D. P. Taylor, "Serotonin Agents in Anxiety," *Annals of the New York Academy of Sciences* vol. 600, entitled: "The Neuropharmacology of Serotonin," pp 545–557, Oct. 15, 1990.) Furthermore, there is evidence that 5-HT$_{1A}$ agents may be useful in the prophylactic treatment of migraine (see: J. Pascual and J. Berciano, "An Open Trial of Buspirone in Migraine Prophylaxis. Preliminary Report," *Clinical Neuropharmacology* 14:3, 1991, pp. 245–250.) Compounds of the present invention are thus envisioned to be useful in the treatment of disorders such as anxiety, panic disorders, obsessive-compulsive disorder, and depression, as well as in the prophylactic treatment of migraine.

In vitro IC$_{50}$ test values for binding to the 5-HT$_{1A}$ receptor were determined for representative compounds of Formula I by the method of S. J. Peroutka, *Brain Research* 344, 167 (1985); with only minor modifications. Test IC$_{50}$ values lower than 100 nM are considered to reflect activity at the 5-HT$_{1A}$ receptor. Compounds with IC$_{50}$ values lower than 20 nM comprise the preferred compounds.

The social interaction task is an in vivo model of anxiety (see: A. P. Guy and C. R. Gardner, "Pharmacological characterization of a modified social interaction model of anxiety in the rat," *Neuropsychobiology* 13: 194–200, 1985.) Compounds of the present invention are active in this in vivo model of anxiety when given subcutaneously in doses of 0.1–1.0 mg/kg, thus providing additional evidence that the present compounds will be useful in the treatment of anxiety and panic disorders.

It is also known that agents which interact with dopaminergic receptors can produce movement disorders and other extrapyramidal side effects (see: R. J. Baldessarini, "Drugs and the Treatment of Psychiatric Disorders," in *"Goodman and Gilman's: The Pharmacologic Basis of Therapeutics,"* 8th ed., p. 428, A. G. Goodman, T. W. Rail, A. S. Nies, and P. Taylor, Editors, Pergamon Press, Inc., Fairview Park, N.Y., 1990). The compounds of the present invention are inactive at the dopaminergic receptors at the doses used to treat disorders such as anxiety, thus the risk of extrapyramidal side effects is small.

In vitro IC$_{50}$ test values for binding to the D$_2$ receptor were determined for representative compounds of Formula I by the method of Burr, Creese, and Snyder, *Molecular Pharmacology* 12, 800 (1976); Creese, Burt, and Snyder, *Science* 196,326 (1977); and Creese, Burt and Snyder, *Science* 192, 481 (1976). Test IC$_{50}$ values greater than 1,000 nM are considered to reflect inactivity at the D$_2$ receptor, indicating the risk of extrapyramidal side effects is small. Compounds with IC$_{50}$ values greater than 1,000 nM comprise the preferred compounds.

Reasonable variations, such as those which would occur to a skilled artisan, may be made herein without departing from the scope of the invention.

We claim:

1. A compound of Formula I or a pharmaceutically acceptable salt thereof, with Formula I being:

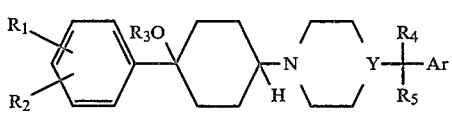

(I)

wherein R$_1$ and R$_2$ are independently selected from H, halogen, CF$_3$, or C$_{1-4}$ alkoxy groups except that R$_1$ and R$_2$ cannot both be H simultaneously, or R$_1$ and R$_2$, when on adjacent carbon atoms, can be taken together to form a

bridge with n being an integer from 1 to 3;
R$_3$ is H or C$_{1-4}$ alkyl;
R$_4$ and R$_5$ are each independently selected from H, C$_{1-4}$ alkyl or phenyl;
Y is CH; and
Ar is an unsubstituted phenyl ring; a substituted phenyl ring of structure II:

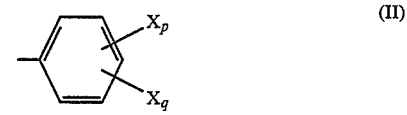

(II)

wherein Xp and Xq may be halogen, nitro, amino, carboxamido, C$_{1-4}$ alkyl, C$_{1-4}$ alkoxy, C$_{1-4}$ haloalkyl, C$_{1-4}$ alkylthio or Xp and Xq can be taken together to form a

(n=1–3); or a heteroaryl group selected from 3-pyridinyl, 4-pyridinyl, 2-thienyl, 2-furanyl, and 1-methyl-2-pyrrolyl moieties.

2. The compound of claim 1 wherein R$_1$ and R$_2$ taken together form the bridge

(n=1–3).

3. The compound of claim 2 wherein each of R$_3$, R$_4$ and R$_5$ is H.

4. The compound of claim 1, Z-1-(1,3-benzodioxol-5-yl)-4-[4-(phenylmethyl)-1-piperidinyl]cyclohexanol.

5. The compound of claim 1, Z-1-(4-fluorophenyl)-4-[4-[(2,5-difluorophenyl)methyl]-1-piperidinyl]-cyclohexanol.

6. The compound of claim 1, Z-1-[4-(1,3-benzodioxol-5-yl)-4-methoxy-1-cyclohexyl]-4-[(3-methoxyphenyl)-methyl]piperidine.

7. The compound of claim 1, Z-1-(4-methoxyphenyl)-4-[4-(phenylmethyl)-1-piperidinyl]cyclohexanol.

8. The compound of claim 1 selected from the group consisting of:
Z-1-1-(1,3-benzodioxol-5-yl)-4-[4(phenylmethyl)-1-piperidinyl]cyclohexanol;
Z-1-(4-fluorophenyl)-4-[4-(phenylmethyl)-1-piperidinyl]cyclohexanol;
Z-1-(4-fluorophenyl)-4-[4-[(3-methoxyphenyl)methyl]-1-piperidinyl]cyclohexanol;
Z-1-(4-fluorophenyl)-4-[4-[(2,5-difluorophenyl)methyl]-1-piperidinyl]cyclohexanol;
Z-1-(1,3-benzodioxol-5-yl)-4-[4-[(2,5-difluorophenyl)-methyl]-1piperidinyl]cyclohexanol; and Z-1-[4-(1,3-benzodioxol-5-yl)-4-methoxy-1-cyclohexyl]-4-[(3-methoxyphenyl)methyl]piperidine.

9. The compound of claim 1 selected from the group consisting of:
Z-1-(1,4-benzodioxan-6-yl)-4-[4-[(3-methoxyphenyl)methyl]-1-piperidinyl]cyclohexanol;
Z-1-(1,3-benzodioxol-5-yl)-4-[4-[(2,5-difluorophenyl)methyl]-1-piperidinyl]cyclohexanol;
Z-1-[4-(1,3-benzodioxol-5-yl)-4-methoxy-1-cyclohexyl]-4-[(3-methoxyphenyl)methyl]piperidine;
Z-1-[4-(1,4-benzodioxan-6-yl)-4-methoxy-1-cyclohexyl]-4-[3-(methoxyphenyl)methyl]piperidine fumarate; and
Z-1-[4-(1,3-benzodioxol-5-yl)-4-methoxy-1-cyclohexyl-4-[(2,5-difluorophenyl)methyl]piperidine fumarate.

10. The compound of claim I selected from the group consisting of:
Z-1-(4-fluorophenyl)-4-[4-(phenylmethyl)-1-piperidinyl]cyclohexanol;
Z-1-(4-fluorophenyl)-4-[4-[(3-methoxyphenyl)methyl]-1-piperidinyl]cyclohexanol; and
Z-1-(4-fluorophenyl)-4-[4-[(2,5-difluorophenyl)methyl]-1-piperidinyl]cyclohexanol.

11. The compound according to claim 1 selected from the group consisting of:
Z-1-(1,3-benzodioxol-5-yl)-4-[4-(phenylmethyl)-1-piperidinyl]cyclohexanol;
Z-1-[4-(1,3-benzodioxol-5-yl)-4-[4-(methoxy-1-cyclohexyl]-4-(3-methoxyphenyl)methyl]piperidine; and
Z-1-(4-fluorophenyl)-4-[4-[(2,5-difluorophenyl)methyl]-1-piperidinyl]cyclohexanol.

12. A pharmaceutical composition comprising an effective anxiolytic amount of a compound of claim 1 and a pharmaceutically acceptable carrier.

13. The composition of claim 12 wherein the compound is Z-1-(1,3-benzodioxol-5-yl)-4-[4-(phenylmethyl)-1-piperidinyl]cyclohexanol.

14. The composition of claim 12 the compound is selected from the group consisting of:
Z-1 -(1,3-benzodioxol-5-yl)-4-[4-(phenylmethyl)-1-piperidinyl]cyclohexanol;
Z-1-(4-fluorophenyl)-4-[4-(phenylmethyl)-1-piperidinyl]cyclohexanol;
Z-1-(1,3-benzodioxol-5-yl)-4-[4-[(2,5-difluorophenyl)methyl]-1-piperidinyl]cyclohexanol;
Z-1-[4-(1,3-benzodioxol-5-yl)-4-methoxy-1-cyclohexyl]-4-[(3-methoxyphenyl)methyl]piperidine;
Z-1-(4-fluorophenyl)-4-[4-[(3-methoxyphenyl)methyl]-1-piperidinyl]cyclohexanol; and
Z-1-(4-fluorophenyl)-4-[4-[(2,5-difluorophenyl)methyl]-1-piperidinyl]cyclohexanol.

15. A method of treating anxiety comprising administering to a patient in need therof an effective amount of a compound of claim 1.

16. The method of claim 15 herein the compound is selected from the group consisting of: Z-1-(1,3-benzodioxol-5-yl)-4-[4-(phenylmethyl)-1-piperidinyl]cyclohexanol; and
Z-1-(4-methoxyphenyl)-4-[4-(phenylmethyl)-1-piperidinyl]cyclohexanol.

17. The method of claim 15 wherein the compound is Z-1-(4-fluorophenyl)-4-[4-[(2,5-difluorophenyl)methyl]-1-piperidinyl]-cyclohexanol.

18. The method of claim 15 wherein the compound is Z-1-[4-(1,3-benzodioxol-5-yl)-4-methoxy-1-cyclohexyl]-4-[(3-methoxyphenyl)methyl]piperidine.

19. The method of claim 15 wherein the compound is selected from the group consisting of:
Z-1-(1,3-benzodioxol-5-yl)-4-[4-(phenylmethyl)-1-piperidinyl]cyclohexanol;
Z-1-(4-fluorophenyl)-4-[4-[(3-methoxyphenyl)methyl]-1-piperidinyl]cyclohexanol;
Z-1-(4-fluorophenyl)-4-[4-[(2,5-difluorophenyl)methyl]-1-piperidinyl]cyclohexanol;
Z-1-(1,3-benzodioxol-5-yl)-4-[4-[(2,5-difluorophenyl)methyl]-1-piperidinyl]cyclohexanol;
Z-1-[4-(1,3-benzodioxol-5-yl)-4-methoxy-1-cyclohexyl]-4-[(3-methoxyphenyl)methyl]-piperidine; and
Z-1-(4-fluorophenyl)-4-[4-(phenylmethyl)-1-piperidinyl]cyclohexanol.

20. The method of claim 19 wherein the compound is selected from the group consisting of:
Z-1-(1,4-benzodioxan-6-yl)-4-[4-[(3-methoxyphenyl)methyl]-1-piperidinyl]cyclohexanol;
Z-1-(1,3-benzodioxol-5-yl)-4-[4-[(2,5-difluorophenyl)methyl]-1-piperidinyl]cyclohexanol;
Z-1-[4-(1,3-benzodioxol-5-yl)-4-methoxy-1-cyclohexyl]-4-[(3-methoxyphenyl)methyl]piperidine;
Z-1-]4-(1,4-benzodioxan-6-yl)-4-methoxy-1-cyclohexyl]-4-[3-(methoxyphenyl)methyl]piperidine fumarate; and
Z-1-]4-(1,3-benzodioxol-5-yl)-4-methoxy-1-cyclohexyl]-4-[(2,5-difluorophenyl)methyl]piperidine fumarate.

21. The method of claim wherein the compound is selected from the group consisting of:
Z-1-(4-fluorophenyl)-4-[4-(phenylmethyl)-1-piperidinyl]cyclohexanol;
Z-1-(4-fluorophenyl)-4-[4-[(3-methoxyphenyl)methyl]-1-piperidinyl]cyclohexanol; and
Z-1-(4-fluorophenyl)-4-[4-[(2,5-difluorophenyl)methyl]-1-piperidinyl]cyclohexanol.

22. A method for the prophylactic treatment of migraines comprising administering to a patient in need thereof an effective amount of a compound of claim 1.

23. The method of claim 22 wherein the compound is selected from the group consisting of: Z-1-(1,3-benzodioxol-5-yl)-4-[(phenylmethyl)-1-piperidinyl]cyclohexanol; and
Z-1-(4-methoxyphenyl)-4-[4-(phenylmethyl)-1-piperidinyl]cyclohexanol.

24. The method of claim 22 wherein the compound is selected from the group consisting of:
Z-1-(1,3-benzodioxol-5-yl)-4-[4-(phenylmethyl)-1-piperidinyl]cyclohexanol;
Z-1-(4-fluorophenyl)-4-[4-(phenylmethyl)-1-piperidinyl]cyclohexanol;
Z-1-(4-fluorophenyl)-4-[4-[(3-methoxyphenyl)methyl]-1-piperidinyl]cyclohexanol;
Z-1-(4-fluorophenyl)-4-[4-[(2,5-difluorophenyl)methyl]-1-piperidinyl]cyclohexanol;
Z-1-(1,3-benzodioxol-5-yl)-4-[4-[(2,5-difluorophenyl)methyl]-1-piperidinyl]cyclohexanol; and
Z-1-[4-(1,3-benzodioxol-5-yl)-4-methoxy-1-cyclohexyl]-4-[(3-methoxyphenyl)methyl]piperidine.

* * * * *